US012728174B2

(12) United States Patent
Edelmann et al.

(10) Patent No.: US 12,728,174 B2
(45) Date of Patent: Sep. 8, 2026

(54) RADIOLABELED MOEM TYPE OLIGONUCLEOTIDES AND PROCESS FOR THEIR PREPARATION

(71) Applicant: Hoffmann-La Roche Inc., Little Falls, NJ (US)

(72) Inventors: Martin Robert Edelmann, Lorrach (DE); Thorsten Muser, Lorrach (DE)

(73) Assignee: Hoffmann-La Roche Inc., Branchburg, NJ (US)

( * ) Notice: Subject to any disclaimer, the term of this patent is extended or adjusted under 35 U.S.C. 154(b) by 1239 days.

(21) Appl. No.: 17/620,232

(22) PCT Filed: Jun. 19, 2020

(86) PCT No.: PCT/EP2020/067058
§ 371 (c)(1),
(2) Date: Dec. 17, 2021

(87) PCT Pub. No.: WO2020/254548
PCT Pub. Date: Dec. 24, 2020

(65) Prior Publication Data

US 2023/0087946 A1 Mar. 23, 2023

(30) Foreign Application Priority Data

Jun. 20, 2019 (EP) .................................... 19181407

(51) Int. Cl.
*A61K 51/04* (2006.01)

(52) U.S. Cl.
CPC ................................ *A61K 51/0491* (2013.01)

(58) Field of Classification Search
CPC ...... C07H 1/00; C07H 21/00; A61K 51/0491; G01N 33/60
See application file for complete search history.

(56) References Cited

U.S. PATENT DOCUMENTS 5,847,104 A 12/1998 Tan et al.
6,737,236 B1 * 5/2004 Pieken .................. C07K 1/063 424/193.1

FOREIGN PATENT DOCUMENTS

WO 2017/021385 A1 2/2017

OTHER PUBLICATIONS

Duconge et al., Bioconjugate Chem., 2008, 19, 1921-1926. (Year: 2008).*

Agrawal, S., et al., "Pharmacokinetics, biodistribution, and stability of oligodeoxynucleotide phosphorothioates in mice" PNAS USA 88(17):7595-7599 (Sep. 1, 1991).

Inkster, J., et al., "Labeling of an Antisense Oligonucleotide with [18F]FPy5yne" Nucleosides, Nucleotides & Nucleic Acids 28(11-12):1131-1143 (Nov. 1, 2009).

"International Preliminary Report on Patentability—PCT/EP2020/067058" (Report Issuance Date: Dec. 21, 2021; Chapter I),:pp. 1-9 (Dec. 30, 2021).

"International Search Report—PCT/EP2020/067058" (w/Written Opinion),:1-16 (Jul. 31, 2020).

Kanayama, N., et al., "Poly(ethylene glycol)-oligodeoxyribonucleotide block copolymers for affinity capillary electrophoretic separation of single-stranded DNAs with a single-base difference" React Funct Polym 67(11):1373-1380 (Nov. 1, 2007).

Kobori, N., et al., "Visualization of mRNA expression in CNS using 11C-labeled phosphorothioate oligodeoxynucleotide" Neuroreport 10(14):2971-2974 (Sep. 29, 1999).

Nair, J., et al., "Multivalent N-acetylgalactosamine-conjugated siRNA localizes in hepatocytes and elicits robust RANi-mediated gene silencing" J Am Chem Soc 136(49):16958-16961 (Dec. 10, 2014).

* cited by examiner

*Primary Examiner* — Michael G. Hartley
*Assistant Examiner* — Leah H Schlientz
(74) *Attorney, Agent, or Firm* — Robert C. Hall; Genentech, Inc.

(57) ABSTRACT

The invention comprises radiolabeled MOEM type oligonucleotide of the formula (I), (I) wherein n, $X^1$, $X^2$, the linker (1), the linker (2), Q* and the receptor targeting moiety are as defined (I) the description. The radiolabeled oligonucleotides of the formula (I) can be used for the determination of the biodistribution and pharmacokinetics of the oligonucleotide in the tissue or body fluid.

(I)

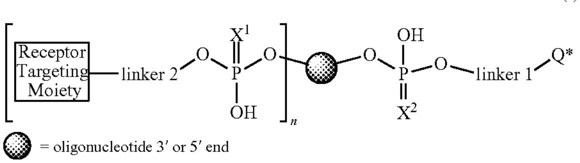

= oligonucleotide 3′ or 5′ end

17 Claims, No Drawings

Specification includes a Sequence Listing.

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide

<400> SEQUENCE: 1

cagagttact tgccaact                                                18
```

<210> SEQ ID NO 2
<211> LENGTH: 13
<212> TYPE: DNA
<213> ORGANISM: Artificial Sequence
<220> FEATURE:
<223> OTHER INFORMATION: Oligonucleotide

<400> SEQUENCE: 2
gcattggtat tca 13

<210> SEQ ID NO 3
<211> LENGTH: 16
<212> TYPE: DNA
<213> ORGANISM: Artificial Sequence
<220> FEATURE:
<223> OTHER INFORMATION: Oligonucleotide

<400> SEQUENCE: 3
gagttacttg ccaact 16

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
ttacacttaa ttatacttcc 20

RADIOLABELED MOEM TYPE OLIGONUCLEOTIDES AND PROCESS FOR THEIR PREPARATION

CROSS-REFERENCE TO RELATED APPLICATIONS

This application is a National Stage Entry under 35 U.S.C. § 371 of International Application No. PCT/EP2020/067058, filed Jun. 19, 2020, which claims benefit to European Application No. 19181407.8, filed on Jun. 20, 2019, each of which is incorporated herein by reference in its entirety and for all purposes.

SEQUENCE LISTING

This application contains a Sequence Listing which has been submitted electronically in ASCII format and is hereby incorporated by reference in its entirety. Said ASCII copy, created on Sep. 9, 2022, is named P35601-US_SeqList_Amended.txt and is 1,113 bytes in size.

SUMMARY OF INVENTION

The invention relates to novel radiolabeled MOEM type oligonucleotide of the formula I

I

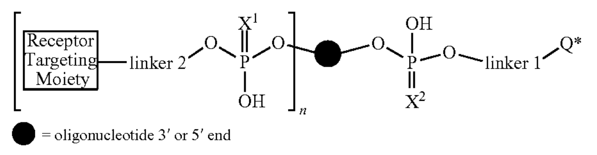

wherein, n, $X^1$ and $X^2$, the linkers 1 and 2, Q* and the receptor targeting moiety are discussed hereinafter, a process for their preparation and to their use for the determination of the biodistribution and pharmacokinetics of the oligonucleotide in the tissue or body fluid.

For an antisense therapeutic approach to be effective, oligonucleotides must be introduced into a patient and must reach the specific tissues to be treated. The biodistribution and pharmacokinetics of a therapeutic drug must be determined as a step preliminary to treatment with the drug. Consequently, there is a need to be able to detect oligonucleotides in body fluids or tissues. Agrawal et al., Clin. Pharmacokinetics 28, 7 (1995), reviews certain aspects of the pharmacokinetics of antisense oligonucleotides. Another well-established approach used in in vivo pharmacokinetic studies of pharmacological compounds such as antisense oligonucleotides entails radiolabeling the compounds to enable detection. In animal models, radiolabeled oligonucleotides have been administered to the animal and their distribution within body fluids and tissues has been assessed by extraction of the oligonucleotides followed by autoradiography (See Agrawal et al., Proc. Natl. Acad. Sci. 88, 7595-7599 (1991).

$^{35}$S-labeling is an established and wide-spread technique. For biological studies, $^{35}$S-labeled oligonucleotide phosphorothioates have been prepared using H-phosphonate chemistry (See Garegg et al., Chem. Scr. 25, 280-282 (1985).

Radioisotopic labeling of synthetic oligonucleotides with $^{14}$C and $^{3}$H is currently accomplished by using the well-established solid-phase automated synthesis. In this approach, the assembly of $^{14}$C or $^{3}$H nucleoside phosphoramidite requires a two-step process as shown in FIG. 1 of U.S. Pat. No. 5,847,104. However, several disadvantages are associated with this method. Since the radioisotope is introduced in the very first step, (a) the radiochemical yield after two steps is limited; (b) this operation often suffers a dilution problem, namely, the natural abundance isotope is usually blended in as a carrier in order to maintain a manageable synthetic scale, resulting in lower specific activity of the final oligos and (c) the phosphoramidite 3 is a reactive species prone to degradation which as the final radioactive precursor leads to stringent storage and transportation requirements.

In view of the deficiencies of the prior art methods other approaches for obtaining radiolabeled oligonucleotides with high specific activity are desirable.

Object of the invention therefore is to provide a new approach for the radiolabeling of oligonucleotides.

It was found that the objective could be fulfilled with the newly developed radiolabeled oligonucleotide of the formula I

I

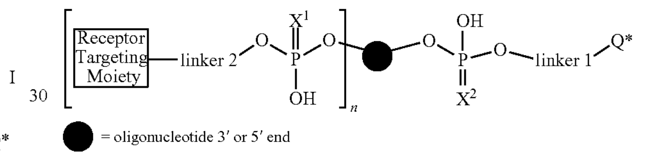

wherein, n is 0 or 1;

$X^1$ and $X^2$ independently of each other are S or O;

linker 1 is a $C_{2-12}$-alkylene bridge, an ethylene glycol bridge containing 1 to 10 ethylene glycol units or a glycerol based bridge of the formula

II

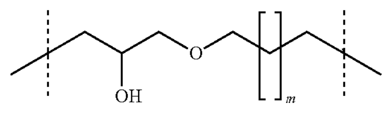

wherein m is an integer of 1 to 6;

linker 2 is an optionally amino group protected amino $C_{2-12}$-alkylene bridge, an amino ethylene glycol bridge containing 1 to 10 ethylene glycol units;

Q* stands for a residue of the formula III

III

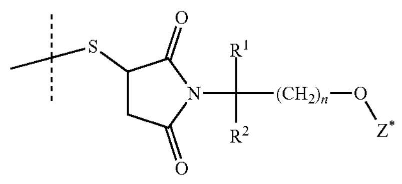

wherein, n is an integer of 1 to 4, $R^1$ and $R^2$ independently of each other are hydrogen, $CF_3$, $C_{1-6}$ alkyl or $R^1$ and $R^2$ together with the carbon atom they are attached to form a $C_{3-5}$-cycloalkane ring;

Z* is a radiolabeled $C_1$-$C_6$ alkyl group; and the receptor targeting moiety is a moiety which adds additional functionality to the oligonucleotide.

The following definitions are set forth to illustrate and define the meaning and scope of the various terms used to describe the invention herein.

The term "$C_{1-6}$-alkyl" denotes a monovalent linear or branched saturated hydrocarbon group of 1 to 6 carbon atoms, and in more particular embodiments 1 to 4 carbon atoms. Examples of $C_{1-6}$-alkyl include methyl, ethyl, propyl, isopropyl, n-butyl, i-butyl, sec-butyl, or t-butyl, preferably methyl or ethyl, more preferably methyl.

The term "$C_{2-12}$-alkyl" likewise denotes a monovalent linear or branched saturated hydrocarbon group of 2 to 12 carbon atoms, in a more particular embodiment 4 to 8 carbon atoms and even more particular embodiment of 6 carbon atoms. Particular examples are butyl, pentyl, hexyl, heptyl or octyl and its isomers, but preferably n-hexyl.

The term $C_{3-5}$-cycloalkane ring stands for a carbocycle of 3 to 5 carbon atoms and includes a cyclopropane-, cyclobutane- or a cyclopentane-ring.

The term "$C_{2-12}$-alkylene bridge" stands for a bivalent linear or branched saturated hydrocarbon group of 2 to 12 carbon atoms, in a more particular embodiment 4 to 8 carbon atoms and in an even more particular embodiment of 6 carbon atoms. Particular examples are butylene, pentylene, hexylene, heptylene or octylene and its isomers, but preferably n-hexylene.

The term "amino $C_{2-12}$-alkylene bridge" stands for a bivalent group comprising an amino group attached to a branched saturated hydrocarbon group of 2 to 12 carbon atoms, in a more particular embodiment 4 to 8 carbon atoms and in an even more particular embodiment of 6 carbon atoms. Particular examples are amino butylene, amino pentylene, amino hexylene, amino heptylene or amino octylene and its isomers, but preferably amino n-hexylene ($-NH-(CH_2)_6-$).

The term "ethylene glycol units" stands for units of the formula-$(CH_2)$ 2-O-which as a bridging unit can contain 1 to 10 ethylene glycol units, preferably 2 to 6 ethylene glycol units.

The term "glycerol unit glycerol based bridge" is characterized by the formula

II

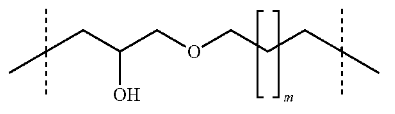

wherein m is an integer of 1 to 6, preferably 1 to 3, more preferably 1.

The term "amino-protecting group" denotes groups intended to protect an amino group and includes benzoyl, benzyloxycarbonyl, carbobenzyloxy (CBZ or Z), 9-fluorenylmethyloxycarbonyl (FMOC), p-methoxybenzyloxycarbonyl, p-nitrobenzyloxycarbonyl, t-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, NY, 1991, chapter 7; E. Haslam, "Protective Groups in Organic Chemistry", J. G. W. McOmie, Ed., Plenum Press, New York, NY, 1973, Chapter 5, and T. W. Greene, "Protective Groups in Organic Synthesis", John Wiley and Sons, New York, NY, 1981.

The term oligonucleotide as used herein is defined as it is generally understood by the skilled person as a molecule comprising two or more covalently linked nucleotides. For use as a therapeutically valuable oligonucleotide, oligonucleotides are typically synthesized as 7 to 30 nucleotides in length.

The oligonucleotides may consist of optionally modified DNA, PNA, RNA or LNA nucleoside monomers or combinations thereof.

The LNA nucleoside monomers are modified nucleosides which comprise a linker group, referred to as a bridge between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, PNA, RNA or LNA nucleoside by the introduction of one or more modifications of the sugar moiety or the nucleo base moiety. In a preferred embodiment the modified nucleoside comprise a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleotides are as a rule linked by a phosphodiester (P═O) and/or a phosphorothioate (P═S) internucleotide linkage which covalently couples two nucleosides together.

Accordingly in some oligonucleotides all internucleotide linkages may consist of a phosphodiester (P═O), in other oligonucleotides all internucleotide linkages may consist of a phosphorothioate (P═S) or in still other oligonucleotides the sequence of internucleotide linkages vary and comprise both phosphodiester (P═O) and phosphorothioate (P═S) internucleotide.

PNA stands for peptide nucleic acids which are composed of the classical nucleobase moieties but instead of the phosphodiester (P═O) or phosphorothioate (P═S) internucleotide linkages contain repeating N-(2-aminoethyl)-glycine units linked by peptide bonds.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}$C (5-methyl cytosine) for LNA nucleoside and with small letters a,t,g,c and $^{Me}$c for DNA nucleosides. Modified nucleobases include but are not limited to nucleobases carrying protecting groups such as t-butylphenoxyacetyl, phenoxyacetyl, benzoyl, acetyl, i-butyryl or dimethylformamidino (see Wikipedia, Phosphoramidit-Synthese, https://de.wikipedia.org/wiki/Phosphoramidit-Synthese of Mar. 24, 2016).

Preferably the oligonucleotide consists of optionally modified DNA or LNA nucleoside monomers or combinations thereof and is 10 to 25 nucleotides in length.

The principles of the oligonucleotide synthesis are well known in the art und well described in literature and public for a like Wikipedia (see e.g. Oligonucleotide synthesis; Wikipedia, the free encyclopedia; https://en.wikipedia.org/wiki/Oligonucleotide_synthesis, of Mar. 15, 2016).

Larger scale oligonucleotide synthesis nowadays is carried automatically using computer controlled synthesizers.

As a rule oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase® HL support from Kinovate.

The oligonucleotide synthesis in principle is a stepwise addition of nucleotide residues to the 5'-terminus of the growing chain until the desired sequence is assembled.

As a rule each addition is referred to as a synthetic cycle and in principle consists of the chemical reactions $a_1$) de-blocking the protected hydroxyl group on the solid support, $a_2$) coupling the first nucleoside as activated phosphoramidite with the free hydroxyl group on the solid support, $a_3$) oxidizing or sulfurizing the respective P-linked nucleoside to form the respective phosphotriester (P═O) or the respective phosphorothioate (P═S);

$a_4$) optionally, capping any unreacted hydroxyl groups on the solid support;

$a_5$) de-blocking the 5' hydroxyl group of the first nucleoside attached to the solid support;

$a_6$) coupling the second nucleoside as activated phosphoramidite to form the respective P-linked dimer;

$a_7$) oxidizing or sulfurizing the respective P-linked dinucleoside to form the respective phosphotriester (P═O) or the respective phosphorothioate (P═S);

$a_8$) optionally, capping any unreacted 5' hydroxyl groups;

$a_9$) repeating the previous steps as to as until the desired sequence is assembled.

The term "radiolabeled" in the context of the present invention is used for the residue Q*, particularly for the substituent Z* which represents a radiolabeled $C_{1-6}$-alkyl group, preferably a radiolabeled $C_{1-4}$-alkyl group, more preferably a radiolabeled methyl or ethyl group, even more preferably a radiolabeled methyl group.

A suitable radiolabeling for these groups therefore means the replacement of the natural hydrogen or carbon atoms by its corresponding radioactive isotopes $^{14}C$ or $^{3}H$, but preferably the replacement of the hydrogen atoms by $^{3}H$.

The term "receptor targeting moiety" stands for a moiety which adds additional functionality to the oligonucleotide.

Such moieties can be selected from any protein receptor target moiety which has the potential to enhance functionality to the oligonucleotide. They include, but are not limited to antibodies or functional peptides or oligonucleotides which target specific molecules like aptamers or non-nucleotide protein receptor target moieties which have the potential to enhance delivery of the oligonucleotide to body tissue or body fluid.

In a preferred embodiment the receptor targeting moiety is an asialoglycoprotein receptor targeting moiety, more preferably a GalNAc moiety.

The GalNAc Moiety has the Formula VII

VII

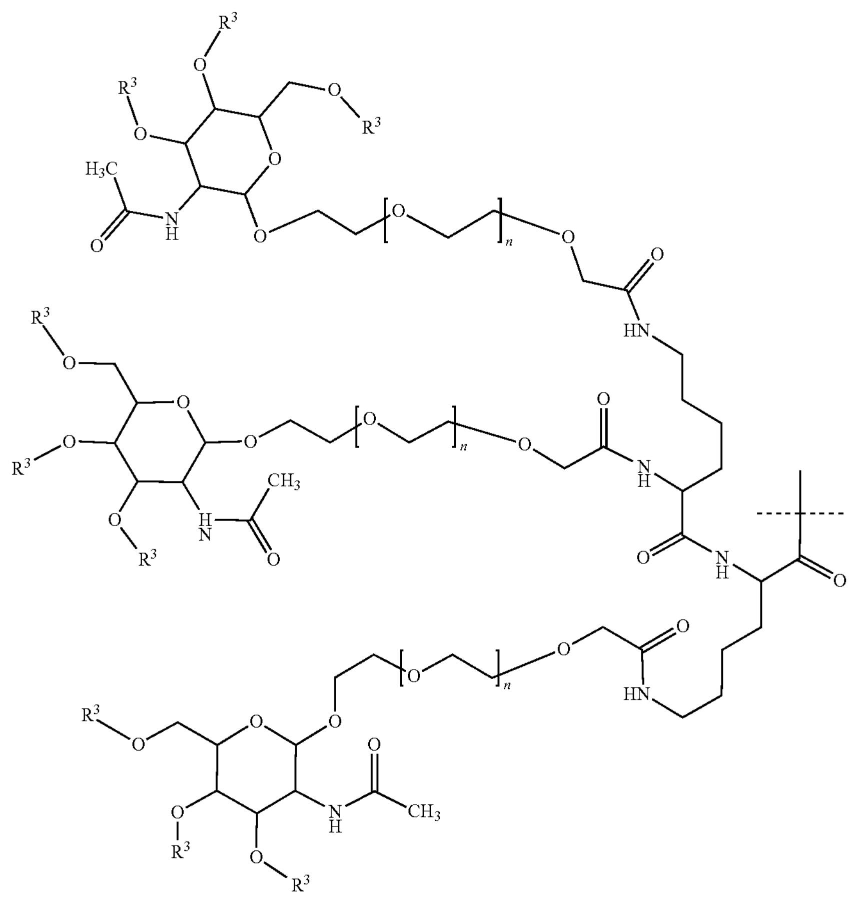

wherein $R^3$ is hydrogen or a hydroxy protecting group and n is an integer from 0 to 10, preferably from 0 to 5, more preferably from 1 to 3, but most preferred is 2, corresponding salts, enantiomers and/or a stereoisomers thereof.

Suitable hydroxy protecting groups are acyl, particularly the $C_{1-12}$-alkylcarbonyl group, more particularly the $C_{1-6}$-alkylcarbonyl group which is optionally substituted by $C_{1-6}$-alkyl or phenyl. More preferred is acetyl, pivaloyl or benzoyl, whereby acetyl is the most preferred hydroxy protecting group.

In a preferred embodiment the GalNAc moiety has the formula VII wherein $R^3$ is hydrogen and n is 2.

The GalNAc moiety is connected with linker 2 via a peptide bond —CO—NH—.

The GalNAc cluster compounds can be prepared according to the PCT Publication WO2017021385.

In a preferred embodiment Q* stands for a residue of the formula III

III

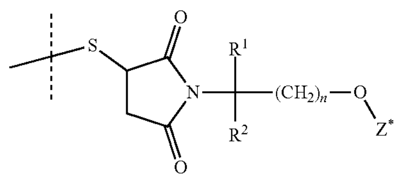

wherein, n is an integer of 1 or 2, more preferably is 1, $R^1$ and $R^2$ independently of each other are hydrogen, $C_{1-2}$-alkyl, preferably methyl, or $R^1$ and $R^2$ together with the carbon atom they are attached form a cyclopropyl ring.

In a Further Preferred Embodiment n is 1 and $R^1$ and $R^2$ are hydrogen or $R^1$ is methyl and $R^2$ is hydrogen or $R^1$ and $R^2$ together form a cyclopropyl ring.

Z* is a radiolabeled $C_{1-4}$-alkyl group, more preferably a radiolabeled methyl or ethyl group, even more preferably a radiolabeled methyl group.

In one embodiment $X^1$ is O and $X^2$ is S. In another embodiment $X^1$ is S and $X^2$ is O, in still another embodiments both $X^1$ and $X^2$ are O or S.

The linker 1 is as outlined above a $C_{2-12}$-alkylene bridge, an ethylene glycol bridge containing 1 to 10 ethylene glycol units or a glycerol based bridge of the formula

II

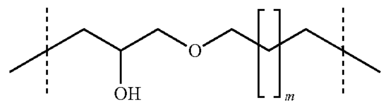

wherein m is an integer of 1 to 6.

The linker 1 more preferably is a $C_{4-8}$-alkylene bridge, even more preferably a $C_6$-alkylene bridge.

The linker 2 is an optionally amino group protected amino $C_{2-12}$-alkylene bridge or an amino ethylene glycol bridge containing 1 to 10 ethylene glycol units;

The linker 2 more preferably is an amino $C_{4-8}$-alkylene bridge, even more preferably an amino-$C_6$-alkylene bridge.

In Another Embodiment the Radiolabeled Oligonucleotide has the Formula Ib

Ib

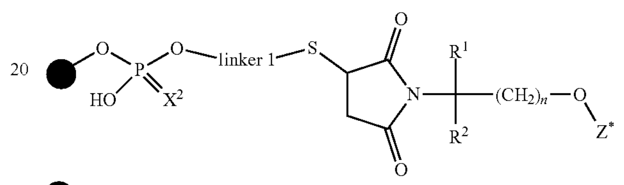

wherein $R^1$, $R^2$, $X^2$, n, Z* and linker 1 are as above and wherein the preferred options outlined above likewise apply.

In a preferred embodiment $X^2$ is S.

In another embodiment the radiolabeled oligonucleotide has the formula Ic

Ic

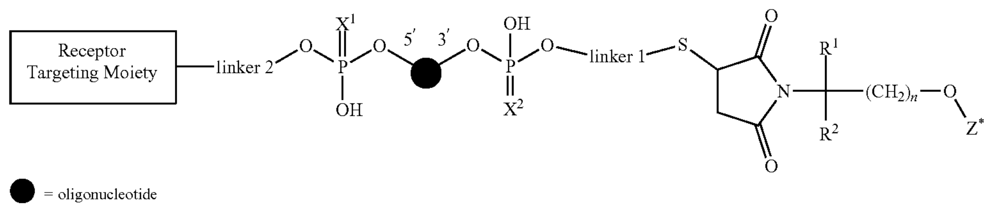

wherein $R^1$ and $R^2$, $X^1$ and $X^2$, n, Z*, linker 1 and linker 2 are as above and wherein the preferred options outlined above likewise apply.

Most preferred embodiments are the radiolabeled oligonucleotide of the formula Ib and Ic.

The radiolabeled oligonucleotide of the formula Ib and Ic can be illustrated with the following compounds.

```
5'-GN2-C6-caG*A*G*t*t*a*c*t*t*g*c*c*a*A*C*T*-C6SH-MOEM

G*C*a*t*t*g*g*t*a*t*T*C*A*-C6SH-MOEM

G*A*G*t*t*a*c*t*t*g*c*c*a*A*C*T*-C6SH-MOEM

5'-MOEM-SH-C6*T*T*A*c*A*c**t*a*a*t*t*a*t*a*c*t*T*C*C
```

wherein C6SH means a C6 (hexylene) thiol linker; MOEM is a $^3H$ labeled N-methoxyethylene maleimide; * stands for phosphorthioate bridges; A,C,G,T are LNA nucleoside monomers and a,t,c,g are DNA nucleoside monomers.

The compounds disclosed herein have the following nucleobase sequence.

```
SEQ ID NO 1:
cagagttacttgccaact

SEQ ID NO 2:
gcattggtattca

SEQ ID NO 3:
gagttacttgccaact

SEQ ID NO 4:
ttacacttaattatacttcc
```

The radiolabeled oligonucleotides of the present invention have a specific activity of 0.037 TBq/mmol (1 Ci/mmol) to 3.7 TBq/mmol (80 Ci/mmol), preferably of 0.111 TBq/mmol (3 Ci/mmol) to 1.85 TBq/mmol (50 Ci/mmol), more preferably of 0.185 TBq/mmol (5 Ci/mmol) to 0.925 TBq/mmol (25 Ci/mmol).

The invention also comprises a process for the preparation of a radiolabeled oligonucleotide of the formula I which comprises the conjugation of a thiol of formula V

V

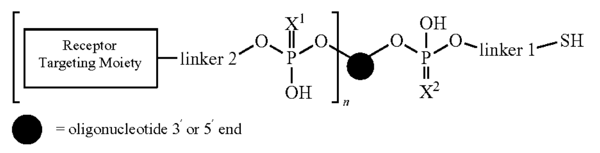

wherein, n is 0 or 1;

$X^1$ and $X^2$ independently of each other are S or O;

linker 1 is a $C_{2-12}$-alkylene bridge, an ethylene glycol bridge containing 1 to 10 ethylene glycol units or a glycerol based bridge of the formula II

II

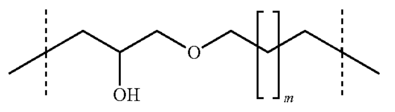

wherein m is an integer of 1 to 6;

linker 2 is an optionally amino group protected amino $C_{2-12}$-alkylene bridge, an amino ethylene glycol bridge containing 1 to 10 ethylene glycol units;

the receptor targeting moiety is a non-nucleotide moiety which adds additional functionality to the oligonucleotide, particularly an asialoglycoprotein receptor targeting moiety, preferably a GalNAc moiety;

with a radiolabeled maleimide compound of formula VI

VI

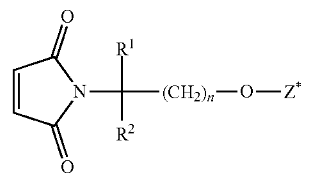

wherein $R^1$ and $R^2$, n and Z* are as above.

The conjugation reaction can be performed in the presence of an organic base and an organic solvent or in an aqueous buffered system at a reaction temperature of 0° C. to 50° C.

Suitable organic bases are tertiary amines such as N,N-diisopropylethylamine (Hünig's base).

Suitable aqueous buffers are for instance phosphate-buffered saline (PBS) having a pH range of 6 to 9.

Suitable solvents are polar aprotic solvents such as N,N-dimethylformamide or dimethylsulfoxide.

The reaction mixture containing the resulting radiolabeled oligonucleotide can be freed from the solvent and the crude can be dissolved in a suitable aqueous buffer solution for further purification.

The purification essentially comprises the steps chromatography, concentration and isolation applying techniques well known to the skilled in then art.

The chromatography is a preparatory HPLC typically with a C-18 reversed-phase column using aqueous and organic solvents as mobile phases.

The concentration of the fractions obtained from the chromatography can take place via a tangential flow filtration, particularly a diafiltration over a suitable membrane.

Finally the isolation of the radiolabeled oligonucleotide from the eluent can typically take place by lyophilization or can be stored in solution.

The syntheses of the radiolabeled maleimide compound of formula VI can follow the reaction scheme outlined below.

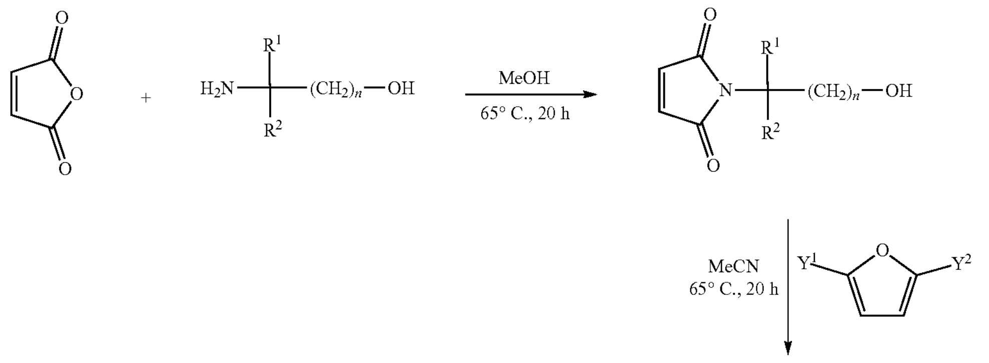

-continued

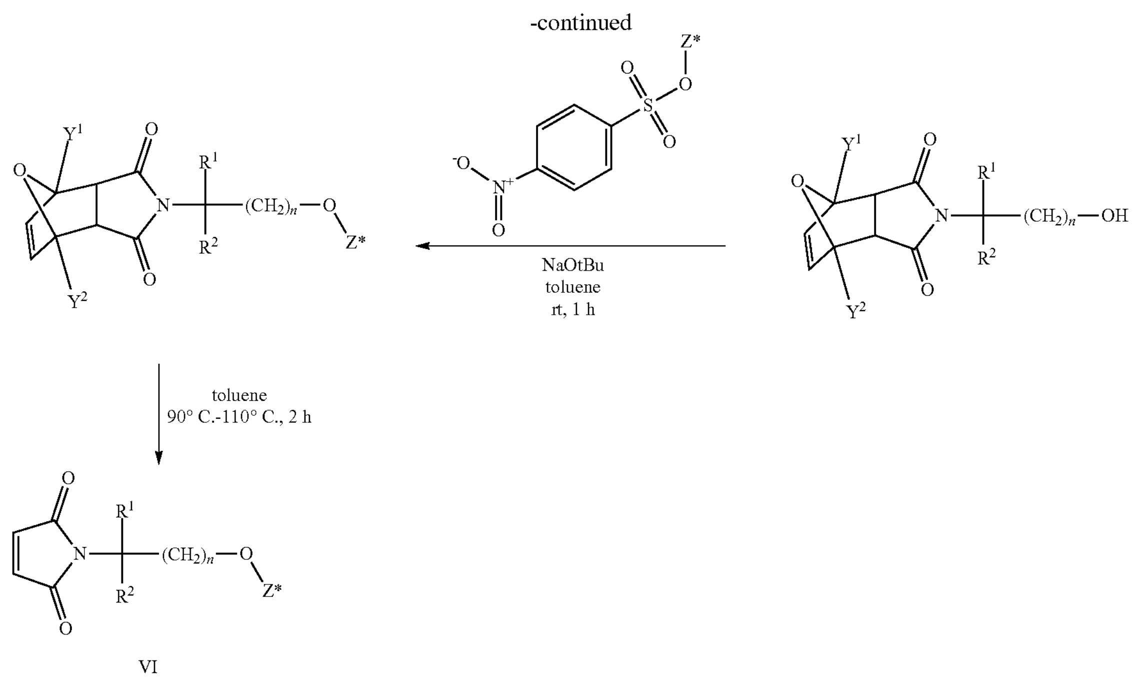

VI $R^1$ and $R^2$, n and Z* are as above and $Y^1$ and $Y^2$ independently of each other are hydrogen or $C_{1-6}$ alkyl. The preferences outlined above likewise apply.

Several methods for the synthesis of maleimide derivatives were reported in literature (N. B. Metha et al, J. Org. Chem., 1960, 25, 1012). A common procedure as depicted in the scheme above involves the condensation of a substituted amine and maleic anhydride, followed by dehydration of the maleamic acid intermediate.

The invention further comprises the use of the radiolabeled oligonucleotide for the determination of the biodistribution and pharmacokinetics of the oligonucleotide in the tissue or body fluid. In addition tritium labeled oligonucleotides can be applied in bioscience, including quantitative whole body autoradiography (QWBA), target binding, and transporter efflux and uptake studies.

The invention also comprises a method for the determination of the biodistribution and pharmacokinetics of an oligonucleotide in the tissue or body fluid comprising a) administering an effective amount of radiolabeled oligonucleotide to the tissue or the body fluid to be examined and
b) measuring the biodistribution and the pharmacokinetics of the radiolabeled oligonucleotide in the tissue or body fluid and optionally
c) imaging the radiolabeled oligonucleotide in the tissue or the body fluid to be examined by autoradiography.

The Invention Further Comprises the Oligonucleotide of the Formula X

X

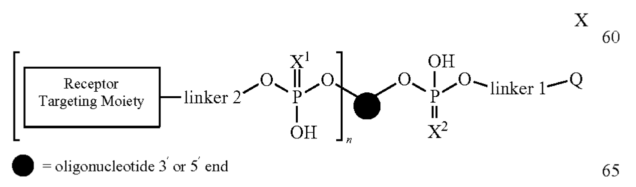

wherein, n is 0 or 1;

$X^1$ and $X^2$ independently of each other are S or O;

linker 1 is a $C_{2-12}$-alkylene bridge, an ethylene glycol bridge containing 1 to 9 ethylene glycol units or a glycerol based bridge of the formula II

II

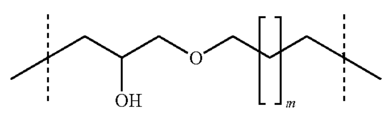

wherein m is an integer of 1 to 6;

linker 2 is an optionally amino group protected amino $C_{2-12}$-alkylene bridge, an amino ethylene glycol bridge containing 1 to 9 ethylene glycol units;

Q stands for a residue of the formula IIIa

IIIa

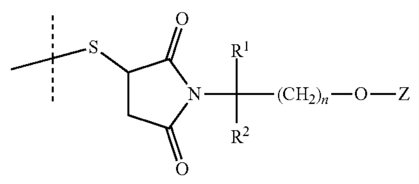

wherein n is an integer of 1 to 4, $R^1$ and $R^2$ independently of each other are hydrogen, $CF_3$, $C_{1-6}$ alkyl or $R^1$ and $R^2$ together with the carbon atom they are attached to form a $C_{3-5}$-cycloalkane ring;

Z is a $C_1$-$C_6$ alkyl group; and the receptor targeting moiety is a moiety which adds additional functionality to the oligonucleotide.

The preferred embodiments described for the radiolabeled oligonucleotides of formula I likewise apply for the non-radiolabeled oligonucleotides of formula X.

Accordingly Q stands for a residue of the formula IIIa

IIIa

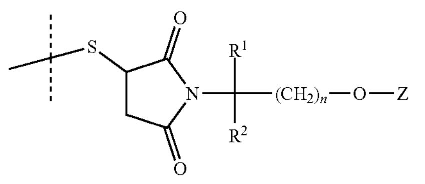

Ib'

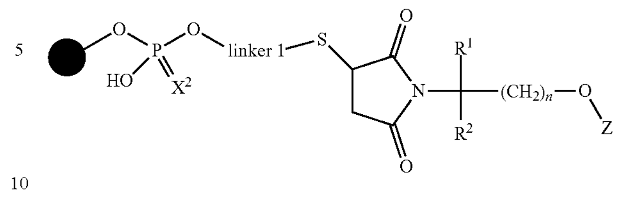

= oligonucleotide, 3' or 5' end wherein $R^1$, $R^2$, $X^2$, n, Z and linker 1 are as above and the preferred options outlined above likewise apply.

In a preferred embodiment $X^2$ is S.

In Another Embodiment the Radiolabeled Oligonucleotide has the Formula Ic'

Ic'

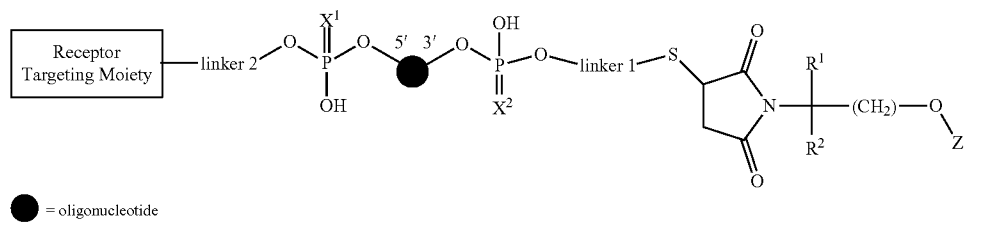

wherein, n is an integer of 1 or 2, more preferably is 1, $R^1$ and $R^2$ independently of each other are hydrogen or $C_{1-6}$ alkyl, more preferably are hydrogen;

Z is a $C_{1-4}$-alkyl group, more preferably methyl or ethyl even more preferably methyl.

In one embodiment $X^1$ is O and $X^2$ is S. In another embodiment $X^1$ is S and $X^2$ is O, in still another embodiments both $X^1$ and $X^2$ are O or S.

The linker 1 is as outlined above a $C_{2-12}$-alkylene bridge, an ethylene glycol bridge containing 1 to 10 ethylene glycol units or a glycerol based bridge of the formula

II

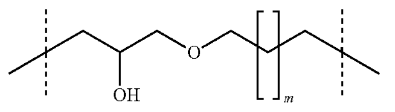

wherein m is an integer of 1 to 6.

The linker 1 more preferably is a $C_{2-8}$-alkylene bridge, even more preferably a $C_6$-alkylene bridge.

The linker 2 is an optionally amino group protected amino $C_{2-12}$-alkylene bridge or an amino ethylene glycol bridge containing 1 to 10 ethylene glycol units;

The linker 2 more preferably is an amino $C_{2-8}$-alkylene bridge, even more preferably an amino-$C_6$-alkylene bridge.

In Another Embodiment the Oligonucleotide has the Formula Ib' wherein, wherein $R^1$ and $R^2$, $X^1$ and $X^2$, n, Z, linker 1 and linker 2 are as above and the preferred options outlined above likewise apply.

EXAMPLES

Abbreviations

Bq Becquerel
Ci curries
Da Dalton
DCM dichloromethane
DI deionized
DIPEA N,N-diisopropylethylamine (Hünig's base)
DMF N, N-dimethylformamide
DMSO dimethylsulfoxide
GBB glycerol based bridge
HV high vacuum
i iso
MeCN acetonitrile
MeOH methanol
min minutes
MOEM methoxyethylene maleimide
MOMCPM 1-(methoxymethyl)cyclopropyl maleimide
MOMEM 1-(2-methoxy-1-methyl-ethyl)maleimide
MS mass spectrometry
MTBE methyl tert-butyl ether
MW molecular weight
MWCO molecular weight cut of
n normal NaOtBu sodium t-butoxide
PBS phosphate-buffered saline
p para
ppm parts per million
QWBA quantitative whole body autoradiography
rpm round per minutes
rt room temperature
SAX strong anion exchange
SCX strong cation exchange
t tertiary
TEA triethylamine
TFA trifluoroacetic acid
THF tetrahydrofurane

General Methods

All oligonucleotides, which were used as starting materials, were synthesized from Roche Pharma research and early development. Tritium labeled [$^3$H]methyl nosylate (triiodomethyl 4-nitrobenzenesulfonate; molar activity: 3 TBq/mmol=80 Ci/mmol) was obtained from RC Tritec (Teufen, CH) as solution in toluene. PBS buffer was purchased from Thermo Fisher Scientific (Paisley, UK), in one (1×) and tenfold (10×) concentration. All other reagents and solvents were obtained from standard commercial sources and used without further purification. Liquid scintillation counting for tritium compounds was accomplished using a HIDEX 300 SL and ULTIMATE GOLD cocktail (PerkinElmer Inc., Waltham, MA, USA).

Analyzes for synthesis of maleimide derivatives were carried out by HPLC Agilent 1260 Infinity II at 220 nm wavelength, Waters XBridge C18, 4.6×150 mm, 3.5 μm column at 40° C. by eluents [A]=water+5% MeCN+0.05% TFA and [B]=MeCN+0.05% TFA by a flow of 1.0 mL/min with the following gradient: 0% [B] to 50% [B] in 10 min and to 80% after 12 min. Oligos 1~4 were determined by UPLC Agilent 1290 at 260 nm wavelength, ACQUITY UPLC Oligonucleotide BEH C18, 2.1×50 mm, 1.7 μm column at 80° C. ([A]=water/methanol/hexafluoro i-propanol/TEA: 950/25/21/2.3 mL; [B]=water/methanol/hexafluoro i-propanol/TEA: 175/800/21/2.3 mL) by a flow of 0.5 mL/min and the following gradient: 10% [B] to 25% [B] in 13 min. Large-scale purification was performed by TELEDYNE (Lincoln, NE, USA) Isco CombiFlash by the use of RediSep® normal-phase Silica Flash Columns (4 g). Solvent [A] was heptane and solvent [B] was methyl t-butyl ether. The column was initially equilibrated at 20% [B] using a flow rate of 18 mL/min, with the absorbance monitored at 214 nm. The elution gradient consisted of isocratic conditions at 20% [B] for 4 minutes, followed by liner gradients to 100% [B] in 14 minutes, and finally isocratic conditions at 100% [B] over 5 minutes. Mass spectrometry was performed by Waters Acquity UPLC H-class System equipped with Single Quadruple (SQ) and ESI Mass Detector. Radiochemical purity was measured using the β-radioactivity HPLC detector RAMONA Quattro with internal solid scintillator (Raytest, Straubenhardt, Germany). Preparative HPLC for MOEM* was performed by Gilson PLC 2020 with XBridge C18 column, 5 μm, 10 mm×250 mm and using water+5% MeCN+0.05% TFA as mobile phase [A] and MeCN+0.05% TFA as mobile phase [B] as gradient with 0% [B] to 70% [B] in 18 min. $^1$H NMR measurements were carried out on a Bruker Avance III 600 MHz spectrometer. The deuterium solvents used was dependent on the product solubility and has been detailed in each case. Chemical shifts are given in ppm with s for singulet, d for doublet, dd for double doublet, m for multiplet, J for indirect dipole-dipole coupling. Concentration was determined by Eppendorf BioSprectrometer® basic at 260 nm wavelength and the corresponding calculated molar extinction coefficient.

Example 1

Synthesis of [$^3$H-methyl]N-methoxyethylene maleimide (MOEM*)

(maleimide compound of formula VI, wherein n=1, $R^1$ and $R^2$=H)

Scheme

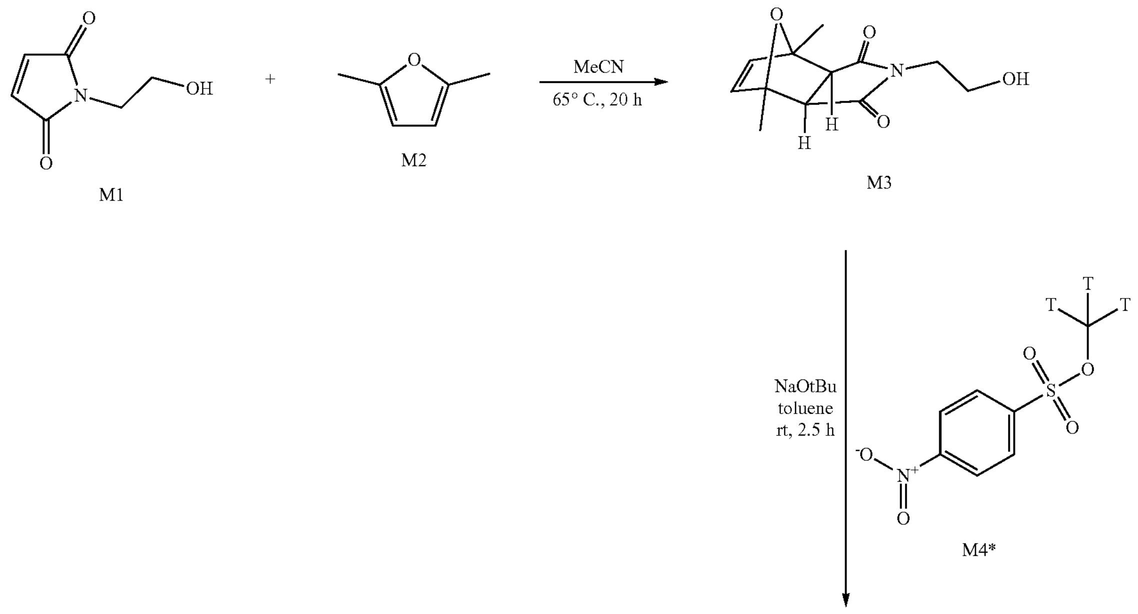

-continued

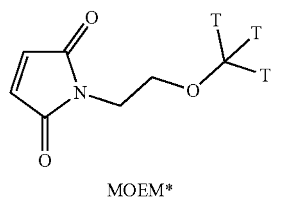
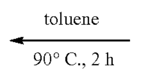

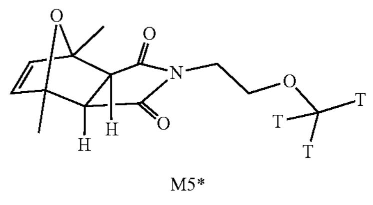

MOEM*

M5* a) Synthesis of exo-4-(2-hydroxyethyl)-1,7-dimethyl-10-oxa-4-aza-tricycle [5.2.1.0$^{2,6}$]dec-8-en-3,5-dione (M3)

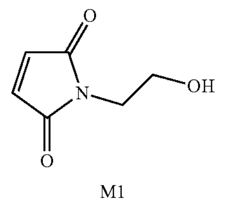

M1

+

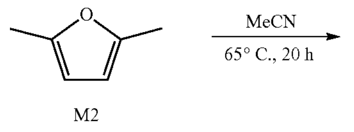

M2

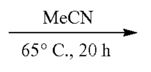

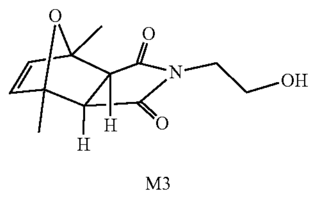

M3

To a solution of commercially available N-(2-hydroxyethyl)maleimide M1 (200 mg, 1.42 mmol) in acetonitrile (2.0 mL) was added at rt 2,5-dimethylfuran M2 (722 mg, 802 μL, 7.51 mmol). The mixture was stirred at 65° C. in a sealed glass tube for 20 h. Removal of the solvent in vacuum and drying in HV gave the crude Diels-Alder adduct M3 as an exo/endo mixture in a 4:1 ratio as a light yellow oil. The endo/exo mixture was purified by Isco flash chromatography to separate the exo derivative in a high purity. Yield (exo): 185 mg (55%). MS (ESI): m/z=238.1 $[M+H]^+$. $^1H$ NMR (DMSO-$d_6$) δ ppm 6.36 (s, 2H), 4.69 (br s, 2H), 3.41 (s, 4H), 2.88 (s, 2H), 1.53 (s, 6H).

b) Synthesis of [3H-methoxy]-exo-4-(2-methoxyethyl)-1,7-dimethyl-10-oxa-4-aza-tricycle [5.2.1.0$^{2,6}$]dec-8-en-3,5-dione (M5*)

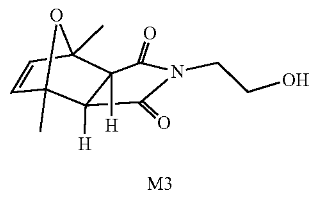

M3

+

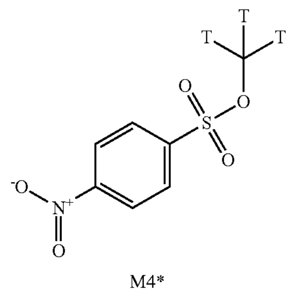

M4*

+

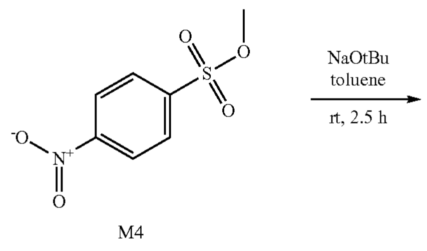

M4

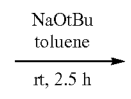

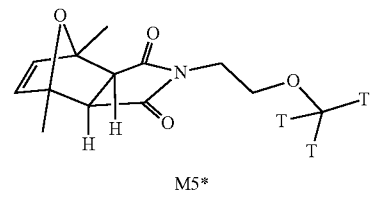

M5*

1.67 GBq (45 mCi) of [$^3$H]-methyl nosylate M4*(125 μg, 0.561 μmol) as solution in toluene was diluted with cold (non-radioactive) methyl 4-nitrobenzenesulfonate M4 (122 μg, 0.561 μmol) in a 1:1 ratio to achieve a specific activity of approximately 40 Ci/mmol. Solution was evaporated, transferred into a sealed tube and concentrated to dryness under an argon flow. To the solid residue (M4*+M4) was added at rt a solution of Diels Alder adduct M3 (666 μg, 2.81 μmol) in 80 μL toluene followed by the addition of 2 M sodium t-butoxide solution in THF (1.7 μL, 3.37 μmol). The mixture was stirred in a sealed tube at rt for 2.5 h. HPLC analysis showed the desired intermediate product M5*with a radiochemical purity of 50%. The reaction mixture was diluted with DCM (1 mL) and directly purified by filtration through a SCX-2/SAX cartridge (Silicycle, 500 mg, pre-conditioned with DCM) to remove basic and acidic compounds. The cartridge was washed with DCM (5 mL) and the resulting solution was concentrated by evaporation to a volume of 100 μL to give the radiolabeled intermediate M5*. The crude solution of M5*was used for the next step without further purification.

c) Synthesis of [3H-methyl]N-methoxyethylene Maleimide (MOEM*)

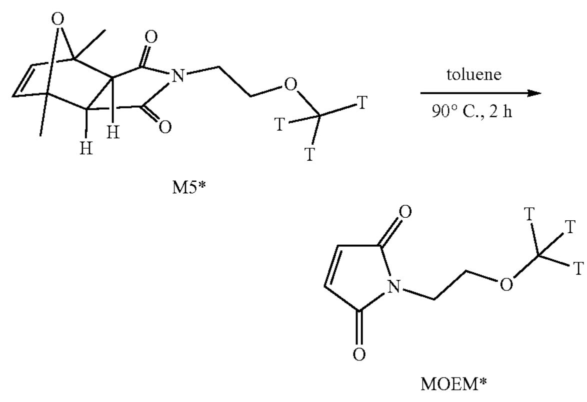

M5*

MOEM*

The obtained crude solution of M5*was transferred into a sealed tube, diluted with toluene (70 μL) and heated at 90° C. for 2 h.

HPLC analysis showed full conversion to the deprotected product MOEM* and remaining unreacted [$^3$H]methyl nosylate M4*. The reaction mixture was allowed to cool to rt and solvent concentrated to dryness under an argon flow. The residue was purified by preparative HPLC to give the desired product [$^3$H-methyl]methoxyethylene maleimide (MOEM*) as a solution in the eluent mixture. The corresponding prep HPLC fraction, containing MOEM* in eluent mixture was directly used for the conjugation with Oligos 1, 2, 3 and 4. Radio yield: 253.5 MBq (6.85 mCi)=15.2%. radio concentration: 34.8 MBq/mL (0.94 mCi/mL), radiochemical purity: 99%. Specific activity could not be determined by MS due to low ionisation. The specific activity was assumed to be 40 Ci/mmol.

Example 2 (Non-Radioactive Conjugation (maleimide compound of formula VI, wherein n=1, $R^1$ and $R^2$=H)

Oligonucleotides Used in the Examples

```
(Oligo 1)
5'-GN2-C6-caG*A*G*t*t*a*c*t*t*g*c*c*a*A*C*T*-C6SH; MW: 7709.5 g/mol;

(Oligo 2)
G*C*a*t*t*g*g*t*a*t*T*C*A*-C6SH; MW: 4537.6 g/mol;

(Oligo 3)
G*A*G*t*t*a*c*t*t*g*c*c*a*A*C*T*-C6SH; MW: 5491.5 g/mol;

(Oligo 4)
5'-SH-C6*T*T*A*c*A*c*t*t*a*a*t*t*a*t*a*c*t*T*C*C; MW: 6742.3 g/mol;
```

General Procedure:

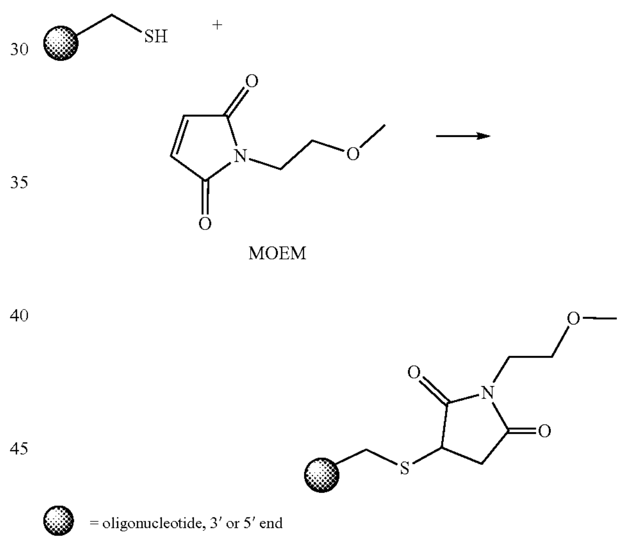

MOEM 1 equivalent of oligonucleotide with 5' or 3' end sulfhydryl linker was dissolved in PBS (volume factor: 250 mL/g). 1.3 equivalent of commercially available methoxyethylene maleimide (MOEM), dissolved in THF (volume factor: 200 mL/g), was added to the aqueous solution and stirred at room temperature for 1 h. UPLC analysis showed a complete addition of maleimide to oligo nucleotide. To exchange the buffer to water, the reaction mixture was transferred into an Amicon® Pro purification system (MWCO: 3.000 Da) and centrifuged at 4000 rpm. DI water was added and the process was repeated 4 times more to complete the exchange. The resulting aqueous solution was lyophilized to isolate the oligonucleotide as a colorless powder with a yield in range of 70%-95% and 90%-99% purity.

In accordance with the general procedure the oligonucleotides (Oligo 1 to 4) have been conjugated with MOEM.

a) Synthesis of conjugate 1 from Oligo 1
5'-GN2-C6-caG*A*G*t*t*a*c*t*t*g*c*c*a*A*C*T*-C6SH-MOEM; Yield: 70%, purity: 90%, MS (m/z): 7859.4 [M-(H)]$^-$ b) Synthesis of conjugate 2 from Oligo 2
G*C*a*t*t*g*g*t*a*t*T*C*A*-C6SH-MOEM; Yield: 93%, purity: 97%, MS (m/z): 4689.5 [M-(H)]$^-$ c) Synthesis of conjugate 3 from Oligo 3
G*A*G*t*t*a*c*t*t*g*c*c*a*A*C*T*-C6SH-MOEM; Yield: 83%, purity: 95%, MS (m/z) 5642.6 [M-(H)]$^-$ d) Synthesis of conjugate 4 from Oligo 4
5'-MOEM-SH-C6*T*T*A*c*A*c*t*t*a*a*t*t*a*t*a*c*t*T*C*C; Yield: 92%, purity: 99%, MS (m/z): 6892.7 [M-(H)]$^-$

Example 3 (Radioactive Conjugation)

(maleimide compound of formula VI, wherein $R^1$ and $R^2$=H)

Oligonucleotides Used in the Examples (Oligo 1)
5'-GN2-C6-caG*A*G*t*t*a*c*t*t*g*c*c*a*A*C*T*-C6SH; MW: 7709.5 g/mol;

(Oligo 3)
G*A*G*t*t*a*c*t*t*g*c*c*a*A*C*T*-C6SH; MW: 5491.5 g/mol;

(Oligo 4)
5'-SH-C6*T*T*A*c*A*c*t*t*a*a*t*t*a*t*a*c*t*T*C*C; MW: 6742.3 g/mol;

General Procedure:

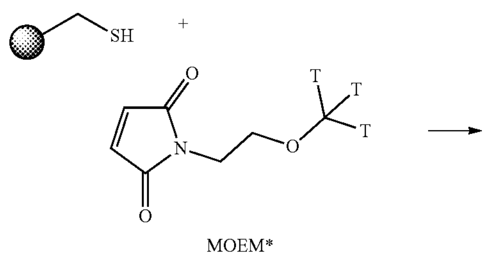

MOEM*

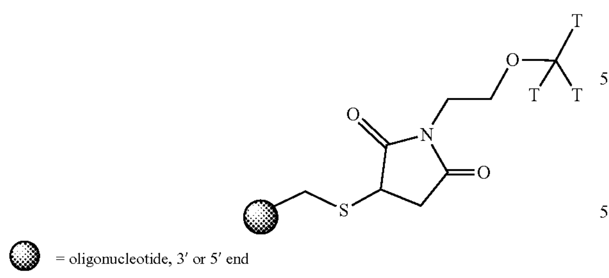

= oligonucleotide, 3' or 5' end 2 equivalents of oligonucleotide with 5' or 3' end sulfhydryl linker was dissolved in PBS (10×) (volume factor: 250 mL/g). 1 equivalent of MOEM*, directly used in prep HPLC eluent with a radio concentration of 35 MBq/mL (0.94 mCi/mL), was added to the aqueous oligonucleotide solution and stirred at room temperature for 1.5 h. UPLC analysis showed a conjugation of MOEM* to oligo nucleotide in range of 30% to 45%, 10 equivalent of cold (non-radioactive) MOEM, dissolved in THF (volume factor: 700 mL/g), was added and stirred at rt for 1 h. UPLC showed a complete conjugation. The reaction mixture was transferred into an Amicon® Pro purification system (MWCO: 3.000 Da) and centrifuged at 4000 rpm. PBS (1×) was added and the process was repeated 4 times to complete a solvent exchange and receive the purified product. The concentration and activity of resulting buffered solution were determined. Radiochemical yields were calculated in range of 69%-72%, specific molar activities could achieve from 0.61 TBq/mmol (16.5 Ci/mmol) to 0.74 TBq/mmol (20.1 Ci/mmol). Radiochemical purities were in range of 96.0% to 98.4%.

In accordance with the general procedure the oligonucleotides, Oligos 1, 3 and 4 have been conjugated.

a) Synthesis of Conjugate 1*[$^3$H]— from Oligo 1

5'-GN2-$C_6$-caG*A*G*t*t*a*c*t*t*g*c*c*a*A*C*T*—C6SH-[$^3$H]-MOEM*; Yield 72%, radiochemical purity: 96.1%, activity: 14.1 MBq (0.38 mCi), specific molar activity: 0.74 TBq/mmol (20.1 Ci/mmol).

b) Synthesis of Conjugate 3*[$^3$H]— from Oligo 3

G*A*G*t*t*a*c*t*t*g*c*c*c*a*A*C*T*—C6SH—[$^3$H]-MOEM; Yield 69%, radiochemical purity: 96.0%, activity: 28.1 MBq (0.76 mCi), specific molar activity: 0.61 TBq/mmol (16.5 Ci/mmol).

c) Synthesis of Conjugate 4*[$^3$H]— from Oligo 4

5'-[$^3$H]-MOEM-SH—C6*T*T*A*c*A*c*t*t*a*a*t*t*a*t*a*c*t*T*C*C; Yield 72%, radiochemical purity: 98.4%, activity: 29.2 MBq (0.79 mCi), specific molar activity: 0.68 TBq/mmol (18.3 Ci/mmol).

Example 4

Synthesis of [$^1H$/$^3H$-Methyl]-1-(Methoxymethyl) Cyclopropyl Maleimide (MOMCPM*)

(maleimide compound of formular VI, wherein $R^1$ and $R^2$ together are cyclopropyl)

-continued

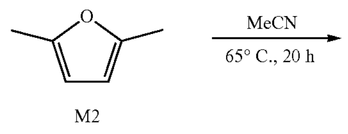

M2

General Scheme

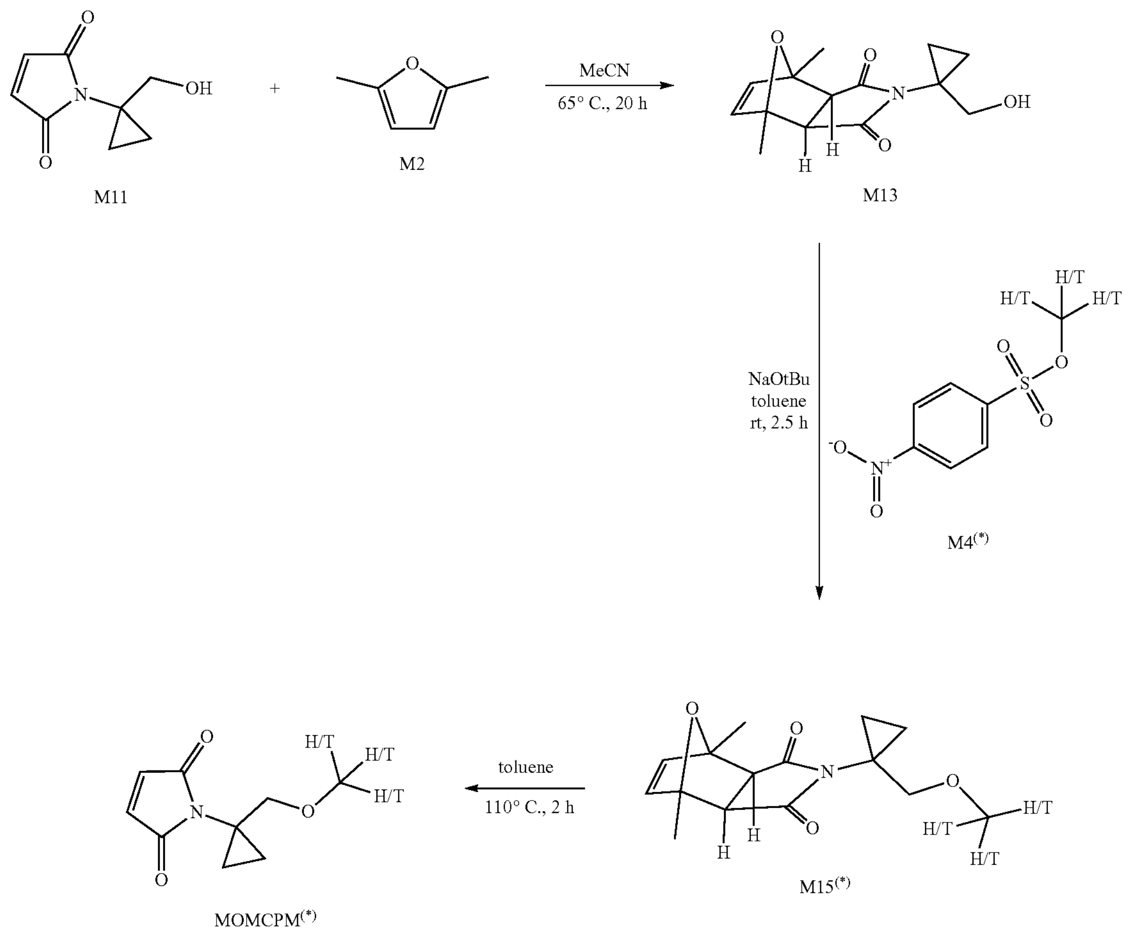

M11 M2 M13 M4(*) M15(*) MOMCPM(*)

a) Synthesis of exo-2-[1-(hydroxymethyl)cyclopropyl]-4,7-dimethyl-3a,7a-dihydro-4,7-epoxyisoindole-1,3-dione (M13)

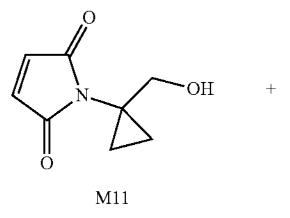

M11

-continued

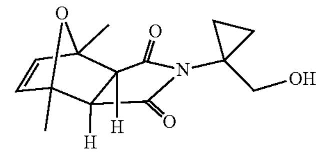

M13

To a solution of commercially available 1-[1-(hydroxymethyl)cyclopropyl]maleimide M11 (209 mg, 1.25 mmol) in acetonitrile (2.0 mL) was added at rt 2,5-dimethylfuran M2 (643 mg, 713 µL, 6.63 mmol). The mixture was stirred at 65° C. in a sealed glass tube for 22 h. Removal of the solvent in vacuum and drying in HV gave the crude Diels-Alder adduct M13 as an exo/endo mixture in a 4:1 ratio as a light yellow oil. The endo/exo mixture was purified by Isco flash chromatography to separate the exo derivative in a high purity.

Yield (exo): 211 mg (64%). MS (ESI): m/z=264.1 $[M+H]^+$. $^1H$ NMR (DMSO-$d_6$) δ ppm 6.35 (s, 2H), 4.70 (br s, 1H), 3.38 (s, 2H), 2.78 (s, 2H), 1.50 (s, 6H), 0.89-0.93 (m, 2H), 0.63-0.67 (m, 2H).

b) Synthesis of exo-2-[1-(methoxymethyl)cyclopropyl]-4,7-dimethyl-3a,7a-dihydro-4,7-epoxyisoindole-1,3-dione (M15)

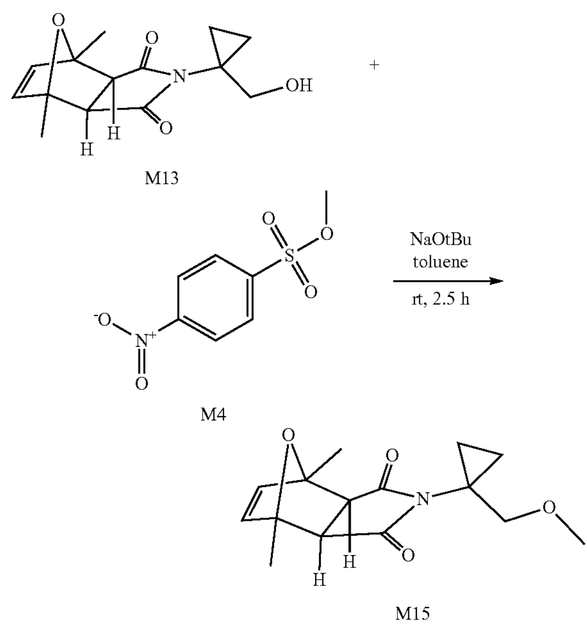

In a sealed tube, methyl nosylate M4 (50 mg, 0.23 mmol) and M13 (72.7 mg, 0.276 mmol) were dissolved in toluene (2.5 mL). The solution was cooled to 0° C. At this temperature, sodium t-butoxide solution (2 M in THF, 403 μL, 806 μmol) was dropped slowly to the reaction solution. The color immediately changed from colorless to dark brown. The ice bath was removed and the mixture was stirred at rt overnight. HPLC analysis showed the desired intermediate product M15. The reaction mixture was diluted with t-butylmethyl ether (30 mL) and extracted with 2 M sodium carbonate (10 mL) and saturated sodium chloride solution (10 mL). The organic phase was dried with sodium sulfate, filtered and evaporated to dryness to get a light yellow liquid. HPLC analysis showed the desired intermediate M15 in a purity of 90%. The crude product was used for the next step without further purification.

b*) Synthesis of [3H-methoxy]-exo-2-[1-(methoxymethyl)cyclopropyl]-4,7-dimethyl-3a,7a-dihydro-4,7-epoxyisoindole-1,3-dione (M15*)

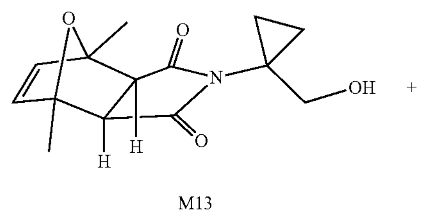

-continued

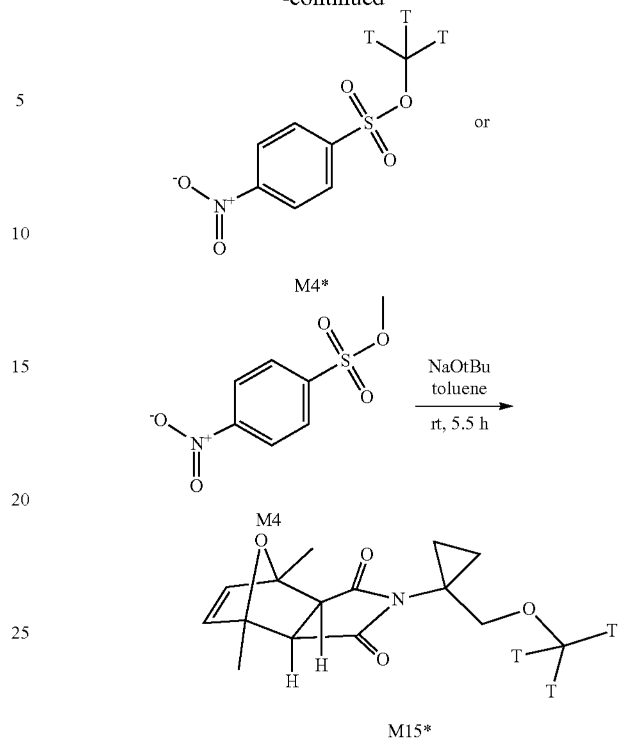

0.93 GBq (25 mCi) of [$^3$H]-methyl nosylate M4*(70 μg, 0.313 μmol) as solution in toluene was diluted with cold (non-radioactive) methyl 4-nitrobenzenesulfonate M4 (68 μg, 0.313 μmol) in a 1:1 ratio to achieve a specific activity of approximately 40 Ci/mmol. Solution was evaporated, transferred into a sealed tube and concentrated to dryness under an argon flow. To the solid residue (M4*+M4) was added at rt a solution of Diels Alder adduct M13 (411 μg, 1.56 μmol) in 80 μL toluene followed by the addition of sodium t-butoxide solution (2 M in THF, 1.0 μL, 1.88 μmol). The mixture was stirred in a sealed tube at rt for 5.5 h. HPLC analysis showed the desired intermediate product M15* with a radiochemical purity of 66%. The reaction mixture was diluted with DCM (1 mL) and directly purified by filtration through a SCX-2/SAX cartridge (Silicycle, 500 mg, preconditioned with DCM) to remove basic and acidic compounds. The cartridge was washed with DCM (5 mL) and the resulting solution was concentrated by evaporation to a volume of 100 μL to give the radiolabeled intermediate M15*.

The crude solution of M15* was used for the next step without further purification.

c) Synthesis of 1-[(1-methoxymethyl)-cyclopropyl] maleimide (MOMCPM)

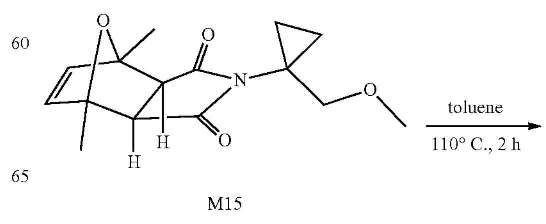

-continued

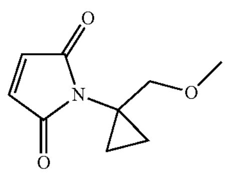

MOMCPM

Crude M15 (30 mg, 108 μmol) was transferred into a sealed tube, dissolved in toluene (4.4 mL) and heated at 110° C. for 2 h. HPLC analysis showed full conversion to the deprotected product MOMCPM. The reaction mixture was allowed to cool to rt and solvent concentrated to dryness under an argon flow. The residue was purified by preparative HPLC to give the desired product MOMCPM as a solution in the eluent mixture. The corresponding preparative HPLC fractions, containing MOMCPM in eluent mixture, were diluted with ethyl acetate (50 mL) and extracted 3× with sodium chloride (30 mL each). The organic phase was dried with sodium sulfate, filtered and evaporated to dryness to give 16 mg (yield 82%) in a purity of 98%.

$^1$H NMR ($CDCl_3$) δ ppm 6.64 (s, 2H), 3.41 (s, 2H), 3.36 (s, 3H), 1.03-1.05 (m, 1H), 0.98-1.00 (m, 2H), 0.92-1.08 (m, 1H)

c*) Synthesis of 1-[(1-methoxy-[$^3$H]-methyl)-cyclopropyl]maleimide (MOMCPM*)

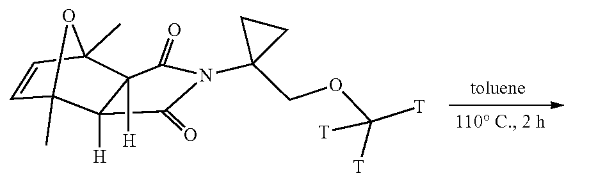

M15*

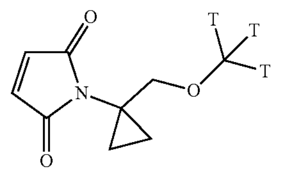

MOMCPM*

The obtained crude solution of M15* was transferred into a sealed tube, diluted with toluene (100 μL) and heated at 110° C. for 2 h.

HPLC analysis showed full conversion to the deprotected product MOMCOM* and remaining unreacted [$^3$H]methyl nosylate M4*. The reaction mixture was allowed to cool to rt and solvent concentrated to dryness under an argon flow. The residue was purified by preparative HPLC to give the desired product 1-[(1-methoxy-[$^3$H]-methyl)-cyclopropyl] maleimide (MOMCPM*) as a solution in the eluent mixture.

The corresponding prep HPLC fraction, containing MOMCPM* in eluent mixture was directly used for the conjugation with Oligos 3 and 4. Radio yield: 140.6 MBq (3.80 mCi)=15.2%. radio concentration: 30.3 MBq/mL (0.82 mCi/mL), radiochemical purity: 99%. Specific activity could not be determined by MS due to low ionisation. The specific activity was assumed to be 40 Ci/mmol.

Example 5 (Non-Radioactive Conjugation)

(maleimide compound of formula VI, wherein n=1, $R^1$ and $R^2$ are cyclopropyl)

Oligonucleotides Used in the Examples

```
(Oligo 3)
G*A*G*t*t*a*c*t*t*g*c*c*a*A*C*T*-C6SH; MW: 5491.5 g/mol;

(Oligo 4)
5'-SH-C6*T*T*A*c*A*c*t*t*a*a*t*t*a*t*a*c*t*T*C*C; MW: 6742.3 g/mol;
```

General Procedure:

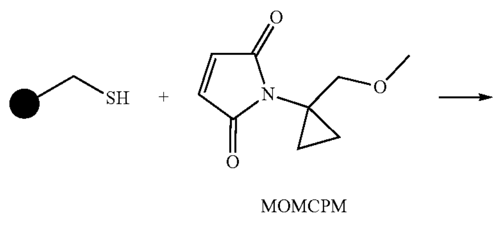

MOMCPM

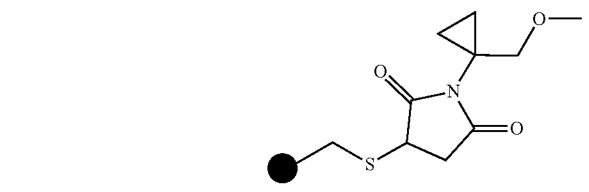

● = oligonucleotide, 3' or 5' end 1 equivalent of oligonucleotide with 5' or 3' end sulfhydryl linker was dissolved in PBS (volume factor: 250 mL/g). 1.3 equivalent of 1-[(1-methoxymethyl)-cyclopropyl]maleimide (MOMCPM), dissolved in THF (volume factor: 200 mL/g), was added to the aqueous solution and stirred at room temperature for 1 h. UPLC analysis showed a complete addition of maleimide to oligo nucleotide. To exchange the buffer to water, the reaction mixture was transferred into an Amicon® Pro purification system (MWCO: 3.000 Da) and centrifuged at 4000 rpm. DI water was added and the process was repeated 4 times more to complete the exchange. The resulting aqueous solution was lyophilized to isolate the oligonucleotide as a colorless powder with a yield in range of 86%-95% and 95%-98% purity.

In accordance with the general procedure the oligonucleotides (Oligo 3, 4) have been conjugated with MOMCPM.

```
a) Synthesis of conjugate 13 from Oligo 3
G*A*G*t*t*a*c*t*t*g*c*c*a*A*C*T*-C6SH-MOMCPM; Yield: 85%, purity: 95%, MS
(m/z): 5668.6 [M-(H)]-

b) Synthesis of conjugate 14 from Oligo 4
5'-MOMCPM-SH-C6*T*T*A*c*A*c*t*t*a*a*t*t*a*t*a*c*t*T*C*C; Yield: 98%, purity:
98%, MS (m/z): 6818.7 [M-(H)]-
```

Example 5 (Radioactive Conjugation)

(maleimide compound of formula VI, wherein n=1, $R^1$ and $R^2$ are cyclopropyl)

Oligonucleotides Used in the Examples

```
(Oligo 3)
G*A*G*t*t*a*c*t*t*g*c*c*a*A*C*T*-C6SH; MW: 5491.5 g/mol;

(Oligo 4)
5'-SH-C6*T*T*A*c*A*c*t*t*a*a*t*t*a*t*a*c*t*T*C*C; MW: 6742.3 g/mol;
```

General Procedure:

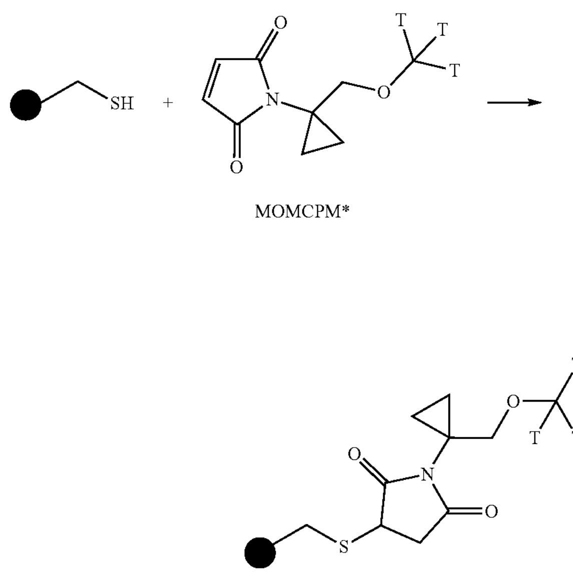

1.2 equivalents of oligonucleotide with 5' or 3' end sulfhydryl linker was dissolved in PBS (10×) (volume factor: 250 mL/g). 1 equivalent of MOMCPM*, directly used in prep HPLC eluent with a radio concentration of 30.3 MBq/mL (0.82 mCi/mL), was added to the aqueous oligonucleotide solution and stirred at room temperature for 2 h. UPLC analysis showed a conjugation of MOMCPM* to oligo nucleotide in range of 26% to 44%, 10 equivalent of cold (non-radioactive) MOMCPM, dissolved in acetonitrile (volume factor: 700 mL/g), was added and stirred at rt for 2 h. UPLC showed a complete conjugation. The reaction mixture was transferred into an Amicon® Pro purification system (MWCO: 3.000 Da) and centrifuged at 4000 rpm. PBS (1×) was added and the process was repeated 4 times to complete a solvent exchange and receive the purified product. The concentration and activity of resulting buffered solution were determined. Radiochemical yields were calculated in range of 90%-799%, specific molar activities could achieve from 0.63 TBq/mmol (17.0 Ci/mmol) to 0.77 TBq/mmol (20.8 Ci/mmol). Radiochemical purities were in range of 97.3% to 98.1%.

In accordance with the general procedure the oligonucleotides, Oligos 3 and 4 have been conjugated with MOMCPM* a) Synthesis of Conjugate 13*[$^3$H]— from Oligo 3

G*A*G*t*t*a*c*t*t*g*c*c*a*A*C*T*-$C_6$SH—[$^3$H]-MOMCPM; Yield 90%, radiochemical purity: 98.1%, activity: 26.2 MBq (0.71 mCi), specific molar activity: 0.63 TBq/mmol (17.0 Ci/mmol).

b) Synthesis of Conjugate 14*[$^3$H]— from Oligo 4

5'-[$^3$H]-MOMCPM-SH—C6*T*T*A*c*A*c*t*t*a*a*t*t*a*t*a*c*t*T*C*C; Yield 99%, radiochemical purity: 97.3%, activity: 34.8 MBq (0.94 mCi), specific molar activity: 0.77 TBq/mmol (20.8 Ci/mmol).

Example 6

Synthesis of [1H/3H-methyl]-1-(2-methoxy-1-methyl-ethyl)maleimide (MOMEM (*)) (maleimide compound of formula VI, wherein n=1, $R^1$=methyl and $R^2$═H)

To a solution of commercially available 1-(2-hydroxy-1-methyl-ethyl)maleimide M21 (132 mg, 0.85 mmol) in acetonitrile (2.0 mL) was added at rt 2,5-dimethylfuran M2 (450 mg, 500 µL, 4.68 mmol). The mixture was stirred at 65° C. in a sealed glass tube for 20 h. Removal of the solvent in vacuum and drying in HV gave the crude Diels-Alder adduct M23 as an exo/endo mixture in a ratio of 4:1 as a light yellow oil with a purity of 98% . . . . The endo/exo mixture was purified by Isco flash chromatography to separate the exo derivative in a high purity. Yield (exo): 123 mg (58%). MS (ESI): m/z=269.2 $[M+NH_4]^+$. $^1H$ NMR (DMSO-$d_6$) δ ppm 6.36 (d, J=1.6 Hz, 2H), 4.54-5.09 (m, 1H), 3.90-4.15 (m, 1H), 3.67 (dd, J=10.8, 8.1 Hz, 1H), 3.49 (dd, J=10.8, 6.4 Hz, 1H), 2.82-2.87 (m, 1H), 2.77-2.81 (m, 1H), 1.53 (d, J=4.0 Hz, 6H), 1.17 (d, J=7.0 Hz, 3H).

General scheme:

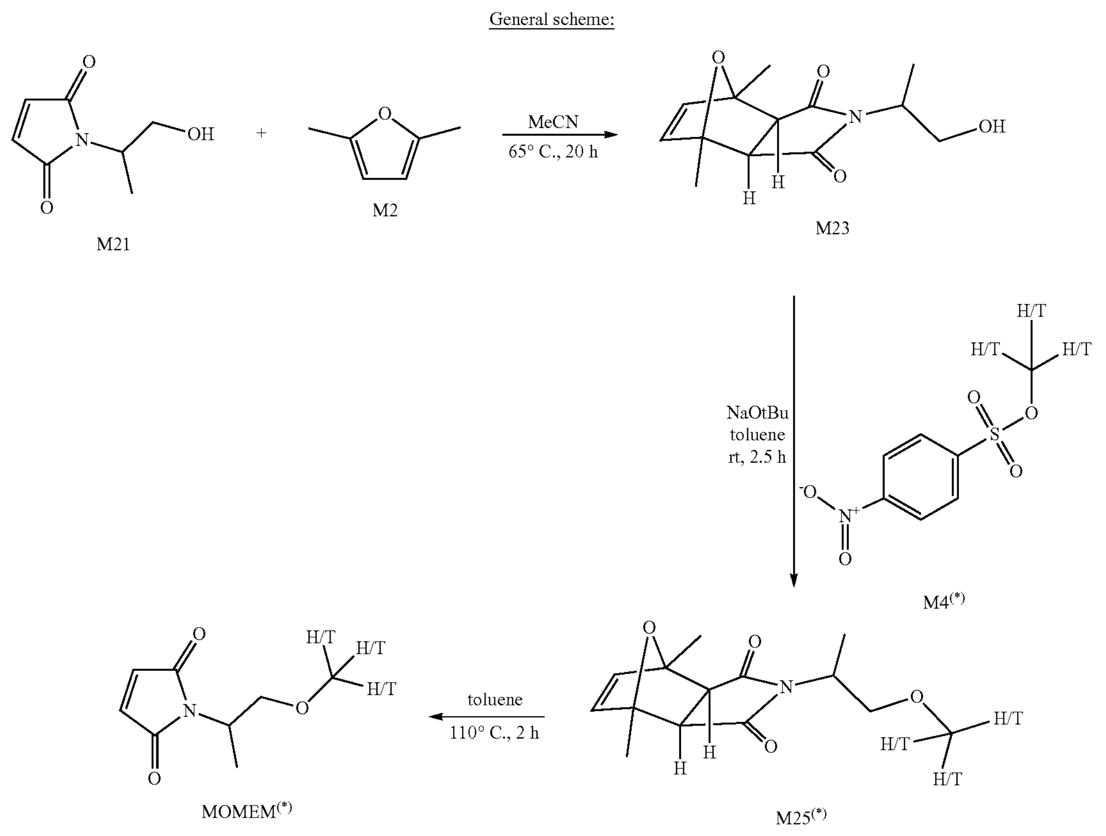

a) Synthesis of exo-4-(2-hydroxy-1-1methyl-ethyl)-4,7-dimethyl-3a,7a-dihydro-4,7-epoxyisoindole-1,3-dione (M23)

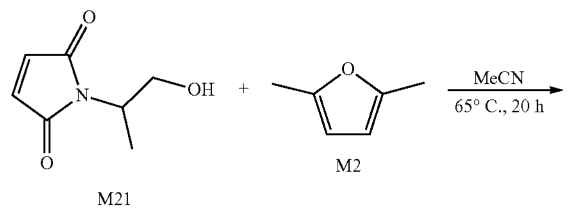

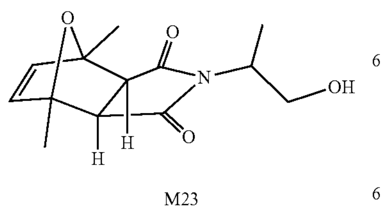

M23 b) Synthesis of exo-2-(2-methoxy-1-methyl-ethyl)-4,7-dimethyl-3a,7a-dihydro-4,7-epoxyisoindole-1,3-dione (M25)

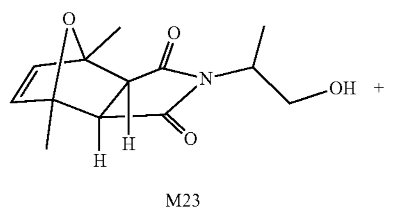

M23

-continued

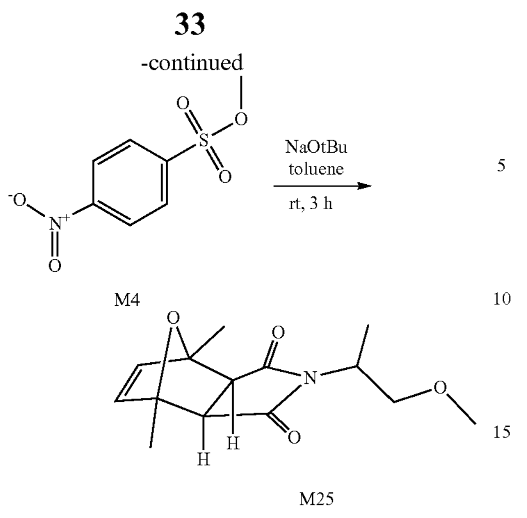

M4

M25

In a sealed tube, methyl nosylate M4 (49.8 mg, 0.23 mmol) and M23 (57.6 mg, 0.23 mmol), dissolved in toluene (2 mL) was cooled to 0° C. Sodium t-butoxide solution (2 M in THF, 138 μL, 0.28 mmol) was added dropwise. The color turned from colorless to brown. The mixture was stirred at room temperature for 3 h. HPLC analysis showed a conversion to the desired intermediate product. The reaction mixture was directly purified by filtration through two SAX-SCX cartridge (Silicycle, 500 mg, pre-conditioned with toluene). The cartridges were washed with toluene (each by 5 mL) and the resulting solution was concentrated by evaporation to dryness to give a colorless oil. The crude product was purified by Isco flash chromatography by a gradient of heptane and MTBE from 0% to 60% MTBE in 15 minutes. Yield: 59 mg (97%). MS (ESI): m/z=266.1 [M+H]+.

$^1$H NMR (DMSO-$d_6$) δ ppm 6.36 (s, 2H), 4.17-4.27 (m, 1H), 3.69 (dd, J=10.0, 8.9 Hz, 1H), 3.69 (dd, J=10.0, 8.9 Hz, 1H), 3.42 (dd, J=9.9, 5.9, 1H), 3.19 (s, 3H), 2.82-2.87 (m, 2H), 1.53 (d, J=3.6 Hz, 6H), 1.19 (d, J=7.1 Hz, 3H).

b*) Synthesis of [3H-methoxy]-exo-2-(2-methoxy-1-methyl-ethyl)-4,7-dimethyl-3a,7a-dihydro-4,7-epoxyisoindole-1,3-dione (M25*)

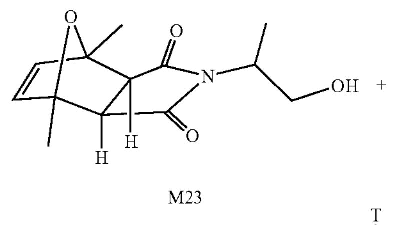

M23

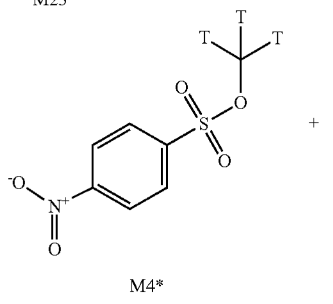

M4*

-continued

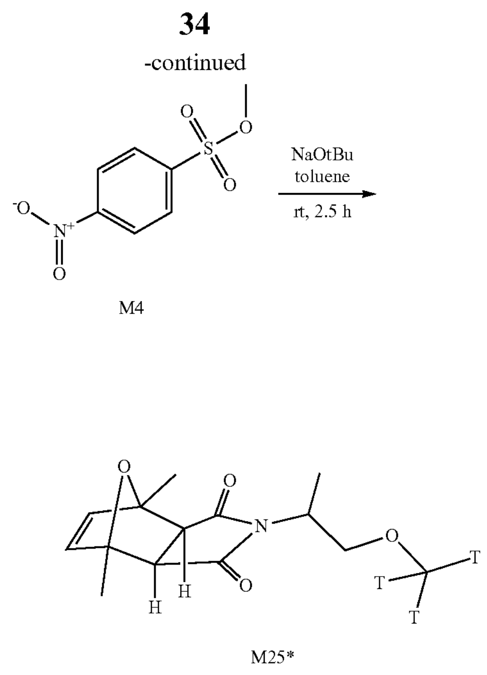

M4

M25*

0.93 GBq (25 mCi) of [$^3$H]-methyl nosylate M4*(70 μg, 0.313 μmol) as solution in toluene was diluted with cold (non-radioactive) methyl 4-nitrobenzenesulfonate M4 (68 μg, 0.313 μmol) in a 1:1 ratio to achieve a specific activity of approximately 40 Ci/mmol. Solution was evaporated, transferred into a sealed tube and concentrated to dryness under an argon flow. To the solid residue (M4*+M4) was added at rt a solution of exo Diels Alder adduct M23 (393 μg, 1.56 μmol) in 80 μL toluene followed by the addition of sodium t-butoxide solution (2 M in THF, 1.0 μL, 1.88 μmol). The mixture was stirred in a sealed tube at rt for 2.5 h. HPLC analysis showed the desired intermediate product M25* with a radiochemical purity of 63%. The reaction mixture was diluted with DCM (1 mL) and directly purified by filtration through a SCX-2/SAX cartridge (Silicycle, 500 mg, pre-conditioned with DCM) to remove basic and acidic compounds. The cartridge was washed with DCM (5 mL) and the resulting solution was concentrated by evaporation to a volume of 100 μL to give the radiolabeled intermediate M25*.

The crude solution of M25* was used for the next step without further purification.

c) Synthesis of 1-(1-methoxy-1-methyl-ethyl)maleimide (MOMEM)

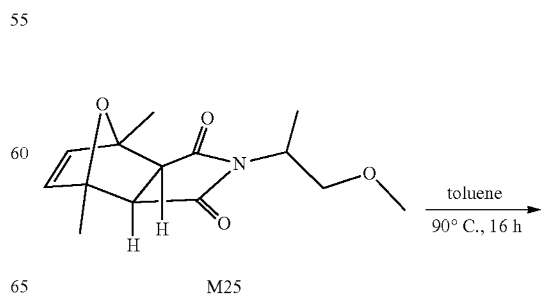

M25

-continued

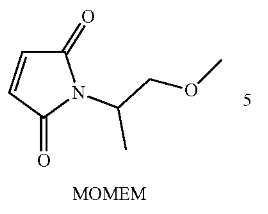

MOMEM 55 mg (0.207 mmol) of M25 was transferred into a sealed tube, dissolved in toluene (500 μL) and heated at 90° C. for 16 h. HPLC analysis showed conversion to the deprotected product MOMEM. The reaction mixture was allowed to cool to rt and solvent concentrated to dryness. The residue was purified by flash chromatography to give the desired product methoxyethylene maleimide (MOMEM) in a purity of >96%, 19 mg (54%) could be isolated as a colorless oil. MS (ESI): m/z=170.08 [M+H]+.

$^1$H NMR (DMSO-$d_6$) δ ppm 6.98 (s, 2H), 4.23 (ddd, J=9.5, 7.1, 5.4 Hz, 1H), 3.67 (t, J=9.8 Hz, 1H), 3.39 (dd, J=10.0, 5.3 Hz, 1H), 3.19 (s, 3H), 1.24 (d, J=7.1 Hz, 3H).

c*) Synthesis of [3H-methyl]-1-(1-methoxy-1-methyl-ethyl)maleimide (MOMEM*)

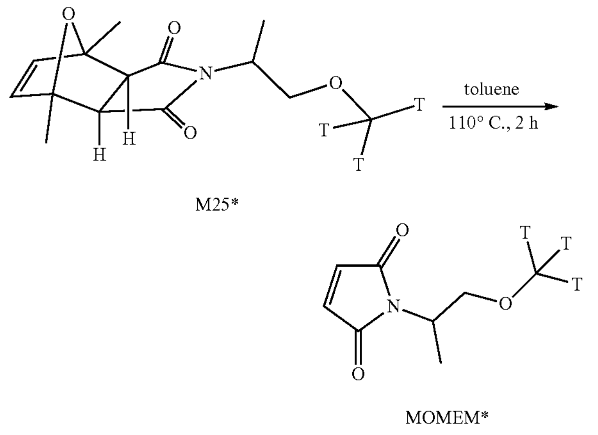

M25*

MOMEM*

The obtained crude solution of M25* was transferred into a sealed tube, diluted with toluene (100 μL) and heated at 110° C. for 2 h.

HPLC analysis showed full conversion to the deprotected product MOMEM* and remaining unreacted [$^3$H]methyl nosylate M4*. The reaction mixture was allowed to cool to rt and solvent concentrated to dryness under an argon flow. The residue was purified by preparative HPLC to give the desired product [3H-methyl]methoxyethylene maleimide (MOMEM*) as a solution in the eluent mixture. The corresponding prep HPLC fraction, containing MOMEM* in eluent mixture was directly used for the conjugation with Oligos 3 and 4. Radio yield: 122.1 MBq (3.3 mCi)=13.2%.

radio concentration: 30.0 MBq/mL (0.81 mCi/mL), radiochemical purity: 99%. Specific activity could not be determined by MS due to low ionisation. The specific activity was assumed to be 40 Ci/mmol.

Example 7 (Non-Radioactive Conjugation)

(maleimide compound of formula VI, wherein n=1, $R^1$=methyl and $R^2$=H)

Oligonucleotides Used in the Examples

```
(Oligo 3)
G*A*G*t*t*a*c*t*t*g*c*c*a*A*C*T*-C6SH; MW: 5491.5 g/mol;

(Oligo 4)
5'-SH-C6*T*T*A*c*A*c*t*t*a*a*t*t*a*t*a*c*t*T*C*C; MW: 6742.3 g/mol;
```

General Procedure:

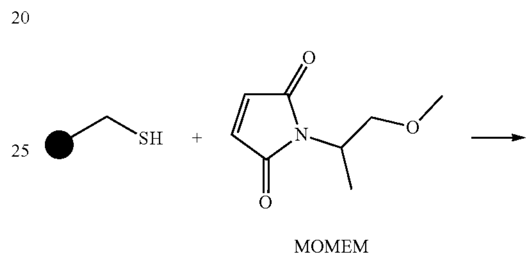

MOMEM

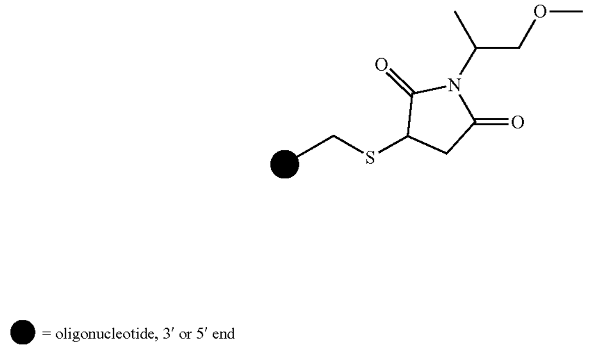

= oligonucleotide, 3' or 5' end 1 equivalent of oligonucleotide with 5' or 3' end sulfhydryl linker was dissolved in PBS (volume factor: 250 mL/g). 1.3 equivalent of 1-(1-methoxy-1-methyl-ethyl)maleimide (MOMEM), dissolved in THF (volume factor: 200 mL/g), was added to the aqueous solution and stirred at room temperature for 1 h. UPLC analysis showed a complete addition of maleimide to oligo nucleotide. To exchange the buffer to water, the reaction mixture was transferred into an Amicon® Pro purification system (MWCO: 3.000 Da) and centrifuged at 4000 rpm. DI water was added and the process was repeated 4 times more to complete the exchange. The resulting aqueous solution was lyophilized to isolate the oligonucleotide as a colorless powder with a yield in range of 83%-98% and 93%-98% purity.

In accordance with the general procedure the oligonucleotides (Oligo 3 and 4) have been conjugated with MOMEM.

```
a) Synthesis of conjugate 13 from Oligo 3
G*A*G*t*t*a*c*t*t*g*c*c*a*A*C*T*-C6SH-MOMCPM; Yield: 85%, purity: 95%, MS
(m/z): 5668.6 [M-(H)]-

b) Synthesis of conjugate 14 from Oligo 4
5'-MOMCPM-SH-C6*T*T*A*c*A*c*t*t*a*a*t*t*a*t*a*c*t*T*C*C; Yield: 98%, purity:
98%, MS (m/z): 6818.7 [M-(H)]-
```

Example 8 (Radioactive Conjugation)

(maleimide compound of formula VI, wherein n=1, $R^1$=methyl and $R^2$=H)

Oligonucleotides Used in the Examples

```
G*A*G*t*t*a*c*t*t*g*c*a*A*C*T*-C6SH;
MW: 5491.5 g/mol; (Oligo 3)

5'-SH-C6*T*T*A*c*A*c*t*t*a*a*t*t*a*t*a*c*t*T*C*C;
MW: 6742.3 g/mol; (Oligo 4)
```

General Procedure:

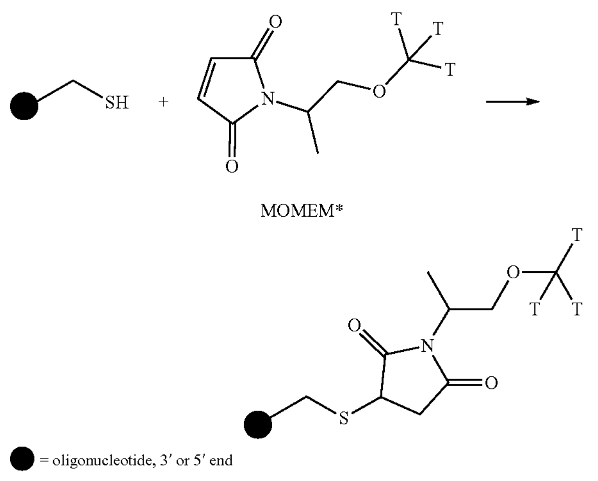

MOMEM*

= oligonucleotide, 3' or 5' end 1.2 equivalents of oligonucleotide with 5' or 3' end sulfhydryl linker was dissolved in PBS (10×) (volume factor: 250 mL/g). 1 equivalent of MOMEM*, directly used in prep HPLC eluent with a radio concentration of 30.0 MBq/mL (0.81 mCi/mL), was added to the aqueous oligonucleotide solution and stirred at room temperature for 2 h. UPLC analysis showed a conjugation of MOMEM* to oligo nucleotide in range of 62% to 66%, 10 equivalent of cold (non-radioactive) MOMEM, dissolved in THF (volume factor: 700 mL/g), was added and stirred at rt for 2 h. UPLC showed a complete conjugation. The reaction mixture was transferred into an Amicon® Pro purification system (MWCO: 3.000 Da) and centrifuged at 4000 rpm. PBS (1×) was added and the process was repeated 4 times to complete a solvent exchange and receive the purified product. The concentration and activity of resulting buffered solution were determined. Radiochemical yields were calculated in range of 87%-89%, specific molar activities could achieve from 0.39 TBq/mmol (10.5 Ci/mmol) to 0.48 TBq/mmol (12.0 Ci/mmol). Radiochemical purities were in range of 93.4% to 94.3%

In accordance with the general procedure the oligonucleotides, Oligos 3 and 4 have been conjugated with MOMEM.

a) Synthesis of Conjugate 23*[$^{3}$H]— from Oligo 3

G*A*G*t*t*a*c*t*t*g*c*c*c*a*A*C*T*—C6SH-[$^{3}$H]-MOMEM; Yield 87%, radiochemical purity: 94.3%, activity: 16.7 MBq (0.45 mCi), specific molar activity: 0.48 TBq/mmol (12.0 Ci/mmol).

b) Synthesis of Conjugate 24*[$^{3}$H]— from Oligo 4

5'-[$^{3}$H]-MOMEM-SH—C6*T*T*A*c*A*c*t*t*t*a*c*t*T*C*C; Yield 89%, radiochemical purity: 93.4%, activity: 14.8 MBq (0.40 mCi), specific molar activity: 0.39 TBq/mmol (10.5 Ci/mmol).

The invention claimed is:

1. Radiolabeled oligonucleotide of the formula I

I

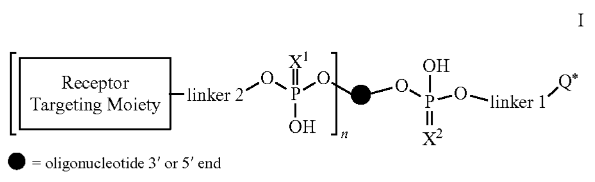

wherein, n is 0 or 1;

$X^1$ and $X^2$ independently of each other are S or O;

linker 1 is a $C_{2-12}$-alkylene bridge, an ethylene glycol bridge containing 1 to 10 ethylene glycol units or a glycerol based bridge of the formula II

II

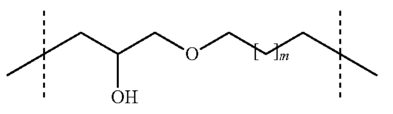

wherein m is an integer of 1 to 6;

linker 2 is an optionally amino group protected amino $C_{2-12}$-alkylene bridge or an amino ethylene glycol bridge containing 1 to 10 ethylene glycol units;

Q* stands for a residue of the formula III

III

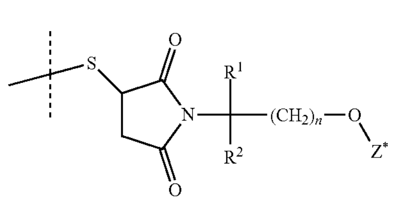

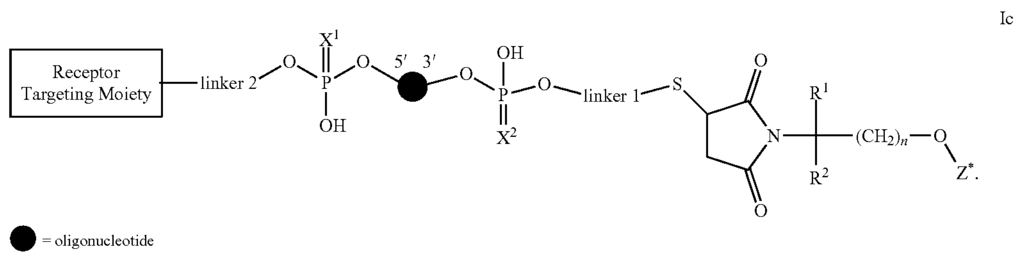

Ic wherein, n is an integer of 1 to 4, $R^1$ and $R^2$ independently of each other are hydrogen, $CF_3$, $C_{1-6}$-alkyl or $R^1$ and $R^2$ together with the carbon atom they are attached to form a $C_{3-5}$-cycloalkane ring;

Z* is a radiolabeled $C_1$-$C_6$ alkyl group; and the receptor targeting moiety is a moiety which adds additional functionality to the oligonucleotide.

2. The radiolabeled oligonucleotide of claim 1, wherein n is an integer of 1.

3. The radiolabeled oligonucleotide of claim 1, wherein $R^1$ and $R^2$ independently of each other are hydrogen or $C_{1-2}$-alkyl; or $R^1$ and $R^2$ together with the carbon atom they are attached to form a cyclopropyl ring.

4. The radiolabeled oligonucleotide of claim 1, wherein Z* is a radiolabeled methyl or ethyl group.

5. The radiolabeled oligonucleotide of claim 4, wherein the radiolabeling is a $^3H$— or a $^{14}C$-labeling.

6. The radiolabeled oligonucleotide of claim 1, wherein the oligonucleotide comprises a contiguous nucleotide sequence of 7 to 30 nucleotides consisting of optionally modified DNA, PNA, RNA or LNA nucleoside monomers or combinations thereof.

7. The radiolabeled oligonucleotide of claim 1 of the formula Ib

Ib

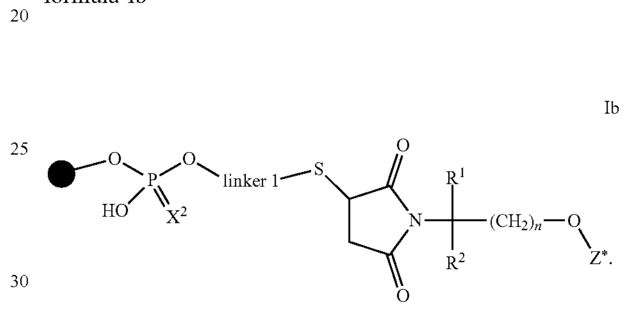

8. The radiolabeled oligonucleotide of claim 1 of the formula Ic

9. The radiolabeled oligonucleotide of claim 1, wherein the receptor targeting moiety is a non-nucleotide moiety.

10. The radiolabeled oligonucleotide of claim 1 having a specific activity of 0.037 TBq/mmol (1 Ci/mmol) to 3.7 TBq/mmol (100 Ci/mmol).

11. The radiolabeled oligonucleotide of claim 4, wherein the radiolabeling is a $^3H$-labeling.

12. The radiolabeled oligonucleotide of claim 1, wherein the receptor targeting moiety is an asialoglycoprotein receptor targeting moiety.

13. The radiolabeled oligonucleotide of claim 1, wherein the receptor targeting moiety is a GalNAc moiety of formula IV

IV

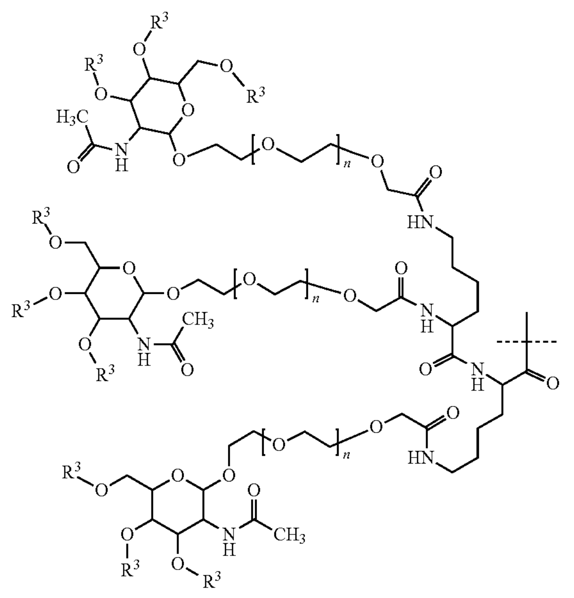

wherein $R^3$ is hydrogen or a hydroxy protecting group and n is an integer from 0 to 10, and corresponding salts, enantiomers and/or a stereoisomers thereof.

14. The radiolabeled oligonucleotide of claim 13, wherein n is an integer from 1 to 3.

15. The radiolabeled oligonucleotide of claim 14, wherein n is an integer of 2.

16. The radiolabeled oligonucleotide of claim 1 having a specific activity of 0.111 TBq/mmol (3 Ci/mmol) to 1.85 TBq/mmol (50 Ci/mmol).

17. The radiolabeled oligonucleotide of claim 1 having a specific activity of 0.185 TBq/mmol (5 Ci/mmol) to 0.925 TBq/mmol (25 Ci/mmol).

* * * * *